US008309353B2

(12) United States Patent
Kume et al.

(10) Patent No.: US 8,309,353 B2
(45) Date of Patent: Nov. 13, 2012

(54) METHOD FOR INDUCTION OF DIFFERENTIATION OF ES CELL

(75) Inventors: Shoen Kume, Kumamoto (JP); Nobuaki Shiraki, Kumamoto (JP); Kahoko Umeda, Kumamoto (JP); Kazuhiko Kume, Kumamoto (JP)

(73) Assignee: Kumamoto University, Kumamoto (JP)

( * ) Notice: Subject to any disclaimer, the term of this patent is extended or adjusted under 35 U.S.C. 154(b) by 112 days.

(21) Appl. No.: 12/602,120

(22) PCT Filed: May 30, 2008

(86) PCT No.: PCT/JP2008/060029
§ 371 (c)(1),
(2), (4) Date: Mar. 31, 2010

(87) PCT Pub. No.: WO2008/149807
PCT Pub. Date: Dec. 11, 2008

(65) Prior Publication Data
US 2012/0058491 A1    Mar. 8, 2012

(30) Foreign Application Priority Data
May 30, 2007   (JP) ................................. 2007-143225

(51) Int. Cl.
C12N 5/00   (2006.01)
C12N 5/02   (2006.01)
C12N 5/07   (2010.01)
C12N 5/10   (2006.01)
C12N 5/071  (2010.01)

(52) U.S. Cl. ........ 435/377; 435/373; 435/325; 435/354; 435/366; 435/370

(58) Field of Classification Search .................... 435/377
See application file for complete search history.

(56) References Cited

FOREIGN PATENT DOCUMENTS
WO   2006/126574   11/2006

OTHER PUBLICATIONS

Shiraki, Embryonic Stem Cells, 2008,26:847-885.*
Extended European Search Report that issued with respect to European Patent Application No. 08777040.0, dated Jul. 30, 2010.
Davila et al., "Use and application of stem cells in toxicology," Toxicol. Sci., vol. 79, pp. 214-23, 2004.
Kulkarni et al., "Functional hepatocyte-like cells derived from mouse embryonic stem cells: A novel in vitro hepatotoxicity model for drug screening," Toxicology In Vitro, vol. 20, pp. 1014-1022, 2006.
Wells et al., "Vertebrate endoderm development," Annu. Rev. Cell Dev. Biol., vol. 15, pp. 393-410, 1999.
Zaret, "Liver specification and early morphogenesis," Mech. Dev., vol. 92, pp. 83-88, 2000.
Jung et al., "Initiation of mammalian liver development from endoderm by fibroblast growth factors," Science, vol. 284, pp. 1998-2003, 1999.
Rossi et al., "Distinct mesodermal signals, including BMPs from the septum transversum mesenchyme, are required in combination for hepatogenesis from the endoderm," Genes & Dev., vol. 15, pp. 1998-2009, 2001.
Deutsch et al., "A bipotential precursor population for pancreas and liver within the embryonic endoderm," Development, vol. 128, pp. 871-881, 2001.
Asahina et al., "Expression of the liver-specific gene Cyp7a1 reveals hepatic differentiation in embryoid bodies derived from mouse embryonic stem cells," Genes to Cells, vol. 9, pp. 1297-1308, 2004.
Heo et al., "Hepatic precursors derived from murine embryonic stem cells contribute to regeneration of injured liver," Hepatology, vol. 44, pp. 1478-1486, 2006.
Teratani et al., "Direct hepatic fate specification from mouse embryonic stem cells," Hepatology, vol. 41, No. 4, pp. 836-846, 2005.
Ishii et al., "In vitro differentiation and maturation of mouse embryonic stem cells into hepatocytes," Exp. Cell Res. vol. 309, pp. 68-77, 2005.
Gouon-Evans et al., "BMP-4 is required for hepatic specification of mouse embryonic stem cell-derived definitive endoderm," Nat. Biotechnol., vol. 24, No. 11, pp. 1402-1411, 2006.
Larsson et al., "Subnuclear localization of WT1 in splicing or transcription factor domains is regulated by alternative splicing," Cell, vol. 81, pp. 391-401, 1995.
Suemori et al., "Efficient establishment of human embryonic stem cell lines and long-term maintenance with stable karyotype by enzymatic bulk passage," Biochem. and Biophys. Res. Commun., vol. 345, pp. 926-932, 2006.
Mohammadi et al., "Structures of the tyrosine kinase domain of fibroblast growth factor receptor in complex with inhibitors," Science, vol. 276, pp. 955-960, 1997.
Shirayoshi et al., "N-Linked oligosaccharides are not involved in the function of a cell-cell binding glycoprotein E-cadherin," Cell Struct. and Funct., vol. 11, pp. 245-252, 1986.
Gu et al., "Global expression analysis of gene regulatory pathways during endocrine pancreatic development," Development, vol. 131, pp. 165-179, 2004.
Yasunaga et al., "Induction and monitoring of definitive and visceral endoderm differentiation of mouse ES cells," Nat. Biotechnol., vol. 23, No. 12, pp. 1542-1550, 2005. Petkov et al., "Gene expression pattern in hepatic stem/progenitor cells during rat fetal development using complementary DNA microarrays," Hepatology, vol. 39, pp. 617-627, 2004.
Kamiya et al., "Oncostatin M and hepatocyte growth factor induce hepatic maturation via distinct signaling pathways," FEBS Lett., vol. 492, pp. 90-94, 2001.
Konig et al., "A novel human organic anion transporting polypeptide localized to the basolateral hepatocyte membrane," Am. J. Physiol. Gastrointest. Liver Physiol., vol. 278, pp. G156-G164, 2000.
International Preliminary Report on Patentability that issued with respect to PCT/JP2008/060029, mailed Jan. 21, 2010.
Shiraki et al., "Guided differentiation of embryonic stem cells into Pdx1-expressing regional-specific defmitive endoderm," Stem Cells, vol. 26(4), pp. 874-885, published online Jan. 31, 2008.

(Continued)

*Primary Examiner* — Valarie Bertoglio
(74) *Attorney, Agent, or Firm* — Greenblum & Bernstein, P.L.C.

(57) ABSTRACT

It is an object of the present invention to establish a system for reliably differentiating an ES cell into a hepatic cell. The present invention provides a method for inducing the differentiation of an ES cell into a hepatic cell, which comprises, in the presence of an M15 cell, culturing a mammal-derived ES cell in the presence of activin and bFGF, and then culturing the ES cell in the presence of dexamethasone, HGF, and oncostatin M.

5 Claims, 13 Drawing Sheets

OTHER PUBLICATIONS

Soto-Gutierrez et al., "Differentiation of mouse embryonic stem cells to hepatocyte-like cells by co-culture with human liver nonparenchymal cell lines," Nat. Protoc., vol. 2(2), pp. 347-356, published online Mar. 8, 2007.

Soto-Gutierrez et al., "Reversal of mouse hepatic failure using an implanted liver-assist device containing ES cell-derived hepatocytes," Nat Biotechnol., vol. 24(11), pp. 1412-1419, published online Nov. 5, 2006.

Dasgupta et al., "E-cadherin synergistically induces hepatospecific phenotype and maturation of embryonic stem cells in conjunction with hepatotrophic factors," Biotechnol Bioeng., vol. 92(3), pp. 257-266, published online Sep. 15, 2005.

Saito et al., "Promoted differentiation of cynomolgus monkey ES cells into hepatocyte-like cells by co-culture with mouse fetal liver-derived cells," World J. Gastroenterol., vol. 12(42), pp. 6818-6827, Nov. 14, 2006.

Lavon et al., "Study of hepatocyte differentiation using embryonic stem cells," J. Cell Biochem., vol. 96(6), pp. 1193-1202, Dec. 15, 2005.

Shiraki et al., "Differentiation of mouse and human embryonic stem cells into hepatic lineages," Genes to Cells, vol. 13(7), pp. 731-746, published online May 30, 2008.

International Search Report dated Sep. 16, 2008 that issued with respect to PCT/JP2008/060029.

* cited by examiner

Fig.13
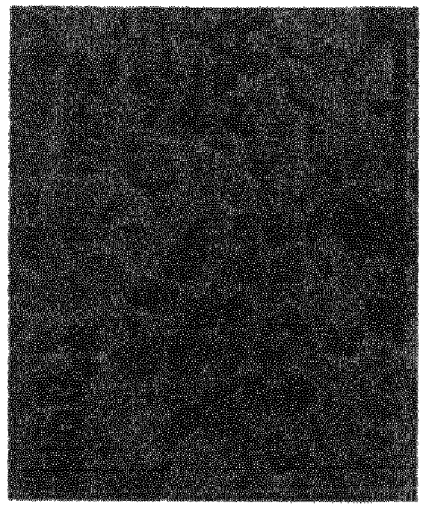
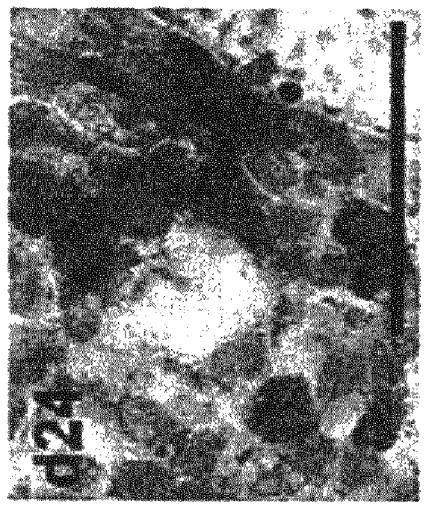

SEQUENCE LISTING

<160> NUMBER OF SEQ ID NOS: 40

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gagtggtgga cagaagcaaa                                                   20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tgaggtagcc atgtccagaa                                                   20

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tcgtattcca acaggagg                                                     18

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
aggcttttgc ttcaccag                                                     18

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cttaaaccga tgggcgatct cact                                              24

```
<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ccccactagc ctctggcaaa at                                              22

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gtgatggtgg gaatgggtca                                                 20

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tttgatgtca cgcacgattt cc                                              22

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gcccaatgtt tagtggagga                                                 20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gacttctcct tctccatgcg                                                 20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
atagagcttt gctgtccccc                                                 20
```

```
<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
cggctttcct tcattctgtc                                              20

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ccctgctgtc tccaacctt                                               19

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tgcgattctc tttcattcgt t                                            21

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gtcctacaga ttgacaatgc                                              20

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cacgctctgg atctgtgaca g                                            21

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ggaactcacc cccaattaca                                              20

<210> SEQ ID NO 18
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gaaggtgagg aagtcgctgt                                              20

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gacggctcag tgttcattc                                               19

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
cttctagctg gtccctctt                                               19

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ggaaggacca cgactcataa c                                            21

<210> SEQ ID NO 22
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gattcttcac aaggtttgtg ttacc                                        25

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
tctgagccct gcatctatct g                                            21

<210> SEQ ID NO 24
<211> LENGTH: 19
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 24
ccccagaggc gttgacata                                                  19

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
tgccaactca gtgaggacaa                                                 20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
tccaacaggc ctgagaaatc                                                 20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gatgtcttcc tgggcatgtt                                                 20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
acatttgctg cccactttc                                                  20

<210> SEQ ID NO 29
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
caggaggaaa ttgatgcagt ttt                                             23

<210> SEQ ID NO 30
<211> LENGTH: 27
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 30
gtcaagatac tccatctgta gcacagt                                27

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
aattccatac ctgggctgtg                                        20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
aggcagcggt ctttgagtta                                        20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
cgagatccct ccaaaatcaa                                        20

<210> SEQ ID NO 34
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
catgagtcct tccacgatac caa                                    23

<210> SEQ ID NO 35
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
tgaacaccgt tggaattgc                                         19

<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence: Synthetic
      primer -continued

```
<400> SEQUENCE: 36
tctctatgag atgtcactgg at                                              22

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
aggtgtgggg gattccccca t                                               21

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gcgatgtggc tgatctgctg c                                               21

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
actgcaacta tcctgacgtg                                                 20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
aggaaatgga ggaagctgtt                                                 20
```

METHOD FOR INDUCTION OF DIFFERENTIATION OF ES CELL

SEQUENCE LISTING

The instant application contains a Sequence Listing which has been submitted in ASCII format via EFS-Web and is hereby incorporated by reference in its entirety. Said ASCII copy, created on Nov. 4, 2011, is named P37658.txt and is 9,411 bytes in size.

TECHNICAL FIELD

The present invention relates to a method for inducing the differentiation of an ES cell. More specifically, the present invention relates to a method for inducing the differentiation of an ES cell into a hepatic cell using a specific supporting cell.

BACKGROUND ART

Embryonic stem (ES) cell is a pluripotent cell derived from the inner cell mass (ICM) of a blastocyst. The ES cell can be unlimitedly cultured in an undifferentiated state, and differentiate into various cell types. According to studies regarding the in vitro differentiation of ES cell, the ES cell can be induced to differentiate into a nerve cell, a hematopoietic cell, and the endodermal cells of the pancreas, liver, and so on. The results of many studies suggest that, since the ES cell is able to recapitulate normal developmental processes, it can be used in the in vitro analysis of induction processes in developmental biology, the cell therapy, the application to hepatotoxicity, and the drug metabolism studies in drug discovery (Non-Patent Documents 1 and 2).

The liver is an important organ having complicated functions such as carbohydrate metabolism, urea and lipid metabolism, the storage of essential nutrition, and biotransformation of drugs. When the toxicity of a metabolite is stronger than that of a parent molecule, the biotransformation of drugs includes bioactivation as well as detoxication. Accordingly, the biotransformation of drugs plays an important role at the initial stage of a drug discovery process. A primary culture has a short lifespan, and thus the culture cannot be maintained for a long period of time. Moreover, the primary culture comprises a large extent of donor-derived mutation. The ES cell is an attractive material because large quantities of cells can always be prepared for the development of a strategy for screening for a novel drug.

The liver of a vertebrate animal develops from the ventral foregut endoderm. In addition to the liver, the lung, pancreas and thyroid also develop from the tissues of the ventral foregut endoderm (Non-Patent Documents 3 and 4). From the results of the previous studies, it was revealed that various sites of the ventral foregut are regionalized by signals from the mesoderm located adjacent to it. However, the mechanism whereby specific endodermal tissues develop has not yet been sufficiently clarified. According to the studies by Wells and Melton, signals from the mesectoderm regionalize the endoderm, and the endoderm then acquires a specific trait. Thereafter, signals derived from the notochord transmit strong signals to the dorsal pancreas. On the other hand, it has been found that FGF and BMP derived from the cardiac mesoderm and the septum transversum mesenchyme are essential for heart induction, the liver gene expression, and the growth of the endoderm (Non-Patent Documents 5 and 6). Cardiac mesoderm-derived FGF signals change the fate of the endoderm to the liver, but not to the pancreas (Non-Patent Document 7).

A study report has revealed that the ES cell had been induced to differentiate into a hepatic cell both in vitro and in vivo. The in vitro method includes the formation of an embryoid body that imitates a microenvironment necessary for the induction of the formation of a hepatic organ (Non-Patent Documents 8 and 9) and treatments with a specific growth factor or cytokine important for the differentiation into hepatocytes (Patent Document 10). Moreover, it has also been revealed that the ES cell differentiates into a hepatic cell by the co-culture of the ES cell and a fetal mesoderm derived cell (Patent Document 11). In recent studies, the in vitro production of stem cells derived from the ES cells using BMP4 has been reported (Non-Patent Document 12). Such study results are promising, but the differentiation into hepatocytes is insufficient. Accordingly, sufficient quantities and qualities of hepatocytes have not yet been produced, so fat Furthermore, Patent Document 1 describes a method for inducing the differentiation of an ES cell into an endodermal cell, which comprises culturing a mammal-derived ES cell in the presence of a supporting cell.

Patent Document 1: International Publication WO2006/126574

Non-Patent Document 1: Davila, J. C., Cezar, G. G., Thiede, M., Strom, S., Mild, T. and Trosko, J. (2004). Use and application of stem cells in toxicology. *Toxicol Sci* 79, 214-23.

Non-Patent Document 2: Kulkarni, J. S. and Khanna, A. (2006). Functional hepatocyte-like cells derived from mouse embryonic stem cells: a novel in vitro hepatotoxicity model for drug screening. *Toxicol In Vitro* 20, 1014-22.

Non-Patent Document 3: Wells, J. M. and Melton, D. A. (1999). Vertebrate endoderm development. *Annu Rev Cell Dev Biol* 15, 393-410.

Non-Patent Document 4: Zaret, K. S. (2000). Liver specification and early morphogenesis. *Mech Dev* 92, 83-8.

Non-Patent Document 5: Jung, J., Zheng, M., Goldfarb, M. and Zaret, K. S. (1999). Initiation of mammalian liver development from endoderm by fibroblast growth factors. *Science* 284, 1998-2003.

Non-Patent Document 6: Rossi, J. M., Dunn, N. R, Hogan, B. L. and Zaret, K. S. (2001). Distinct mesodermal signals, including BMPs from the septum transversum mesenchyme, are required in combination for hepatogenesis from the endoderm. *Genes Dev* 15, 1998-2009.

Non-Patent Document 7: Deutsch, G., Jung, J., Zheng, M., Lora, J. and Zaret, K. S. (2001). A bipotential precursor population for pancreas and liver within the embryonic endoderm. *Development* 128, 871-81.

Non-Patent Document 8: Asahina, K., Fujimori, H., Shimizu-Saito, K., Kumashiro, Y., Okumura, K., Tanaka, Y., Teramoto, K., Arii, S. and Teraoka, H. (2004). Expression of the liver-specific gene Cyp7a1 reveals hepatic differentiation in embryoid bodies derived from mouse embryonic stem cells. *Genes Cells* 9, 1297-308.

Non-Patent Document 9: Heo, J., Factor, V. M., Uren, T., Takahama, Y., Lee, J. S., Major, M., Feinstone, S. M. and Thorgeirsson, S. S. (2006). Hepatic precursors derived from murine embryonic stem cells contribute to regeneration of injured liver. *Hepatology* 44, 1478-86.

Non-Patent Document 10: Teratani, T., Yamamoto, H., Aoyagi, K., Sasaki, H., Asari, A., Quinn, G., Sasaki, H., Terada, M. and Ochiya, T. (2005). Direct hepatic fate specification from mouse embryonic stem cells. *Hepatology* 41, 836-46.

Non-Patent Document 11: Ishii, T., Yasuchika, K., Fujii, H., Hoppo, T., Baba, S., Naito, M., Machimoto, T., Kamo, N., Suemori, H., Nakatsuji, N. et al. (2005). In vitro differentiation and maturation of mouse embryonic stem cells into hepatocytes. *Exp Cell Res* 309, 68-77.

Non-Patent Document 12 : Gouon-Evans, V., Boussemart, L., Gadue, P., Nierhoff, D., Koehler, C. I., Kubo, A., Shafritz, D. A. and Keller, G. (2006). BMP-4 is required for hepatic specification of mouse embryonic stem cell-derived definitive endoderm. *Nat Biotechnol* 24, 1402-11.

BRIEF DESCRIPTION OF DRAWINGS

FIG. 1(A) shows the quantification of the terminally differentiated endoderm (E-cadherin+/Cxcr4+) or Pdxl//GFP-expressing cells by a flow cytometry analysis. ES cells were cultured on M15 cells, and from d0 to d4, activin and bFGF were added to the culture. From d4 to d8, various combinations of soluble factors were added thereto, and the obtained mixture was then cultured in a culture solution containing FBS or KSR, in which a glucose concentration was altered (2,000 or 4,000 mg/L). On d8, the ratio between the terminally differentiated endodermal cells defined as E-cadherin+/Cxcr4+and Pdxl-expressing cells was evaluated by a flow cytometry analysis. FIG. 1(B) shows the real-time PCR analysis results of the relative levels of Shh and Afp transcriptions in the terminally differentiated endodermal cells (E-cadherin+/Cxcr4+) in the differentiated ES cells. cDNA derived from terminally differentiated endodermal cell which had been sorted with a flow cytometer, was used as a template. The Shh and Afp transcription levels were quantified by comparing them with the level of β-actin, and they were standardized. The obtained results were compared with those of a control in 4,500 FBS (ES cells differentiated under conditions in which 4,500 mg/L glucose and 10% FBS were added, but growth factors were not added). The value of the control was defined as 1. (A and B): control (white, no growth factors); activin & bFGF (black, 20 ng/mL activin and 50 ng/mL bFGF); Dex & HGF& OsM (gray, 1 mM dexamethasone, 10 ng/mL HGF, 10 ng/mL oncostatin M); 2,000 FBS (2,000 mg/L glucose, 10% FBS); 2,000 KSR (2,000 mg/L glucose, 10% KSR); 4,500 FBS (4,500 mg/L glucose, 10% FBS); 4,500 KSR (4,500 mg/L glucose, 10% KSR).

FIG. 2(A) shows a comparison among the actions of various factors added from d4 to d8. ES cells were cultured on M15 cells, and from d0 to d4, activin and bFGF were added to the culture. From d4 to d8, activin and bFGF were removed. Thereafter, the following culture conditions were then analyzed. A control (no factors), activin & bFGF (activin and bFGF), or Dex & HGF & OsM (Dex, HGF, and OsM) was added to the cells, and the obtained mixture was then cultured in a culture solution containing KSR or FBS having a glucose concentration of 2,000 mg/L or 4,500 mg/mL (2,000 FBS, 2,000 KSR, 4,500FBS, or 4,500 KSR). FIG. 2(B) shows a comparison made among the effects of Dex, HGF, and OsM, which had been added form d4 to d8. The upper view shows a case in which none of the three factors were added from d4 to d8. The lower view shows a case in which any two of the three factors were added. FIG. 2(C) shows that the expression of an Alb protein (green) was detected on d30 under the conditions in (B). In (A and B), the ES cells were cultured for 8days and were then stained with AFP (red) and GFP (Pdxl: green). In (A, B, and C), the bar indicates 200 μm.

FIG. 11(A) shows the RT-PCR analysis of the endoderm or hepatic marker in the differentiated ES cells. The term "hES" indicates undifferentiated human ES cells; the terms "d18" and "d30" indicate undifferentiated human ES cells on day 18 and 30, which had been allowed to grow on M15 cells; and the term "M15" indicates M15 cells. FIG. 11(B) shows that the differentiated ES cells on d14, d18, and d30 were stained with AFP (green) and albumin (red).

FIG. 13 shows a large number of hepatic cells having collagen cytoplasmic storage (strong red) in colonies, detected by the PAS staining of the differentiated ES cells on d24 and d50. The bar indicates 200 μm.

DISCLOSURE OF THE INVENTION

Figure 1:
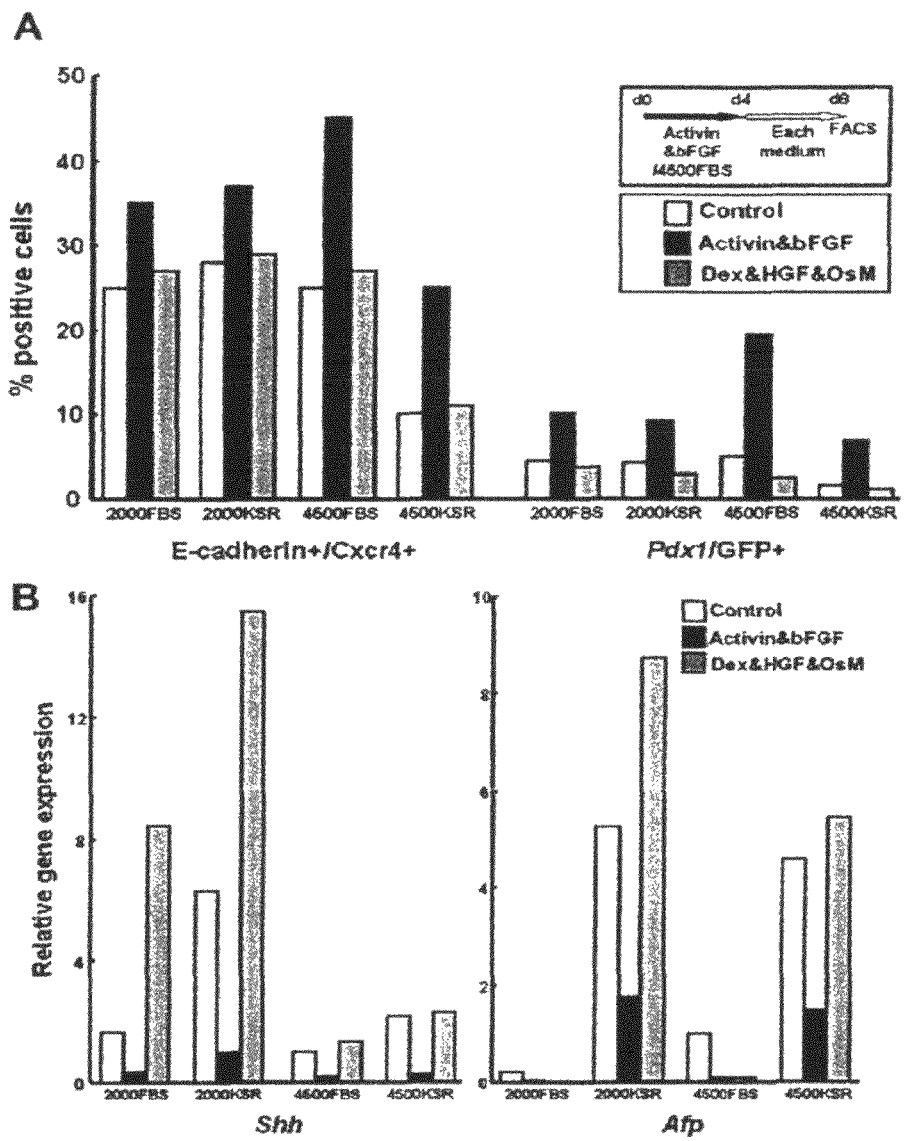
FIG. 1 shows that mouse ES cells were efficiently differentiated, not into Pdxl-expressing cells but into Afp-expressing liver endodermal cells, by modifying the conventional ES cell differentiation protocols.

Problems to be Solved by the Invention

It is an object of the present invention to establish a system for reliably differentiating an ES cell into a liver cell.

Means for Solving the Problems

As a result of intensive studies directed towards achieving the aforementioned object, the present inventors have found that, using an M15 cell as a supporting cell, a mammal-derived ES cell can be induced to differentiate into a liver cell by culturing the mammal-derived ES cell in the presence of activin and bFGF, and then culturing the ES cell in the presence of dexamethasone, HGF, and oncostatin M. Thus, the inventors have completed the present invention.

The present invention provides a method for inducing the differentiation of an ES cell into a liver cell, which comprises, in the presence of an M15 cell, culturing a mammal-derived ES cell in the presence of activin and bFGF, and then culturing the ES cell in the presence of dexamethasone, HGF, and oncostatin M.

Preferably, BMP4 is further added to the culture system, when the mammal-derived ES cell is cultured in the presence of the M15 cell.

Preferably, after the ES cell has been cultured in the presence of activin and bFGF, activin and bFGF is removed, and the ES cell is then cultured in the presence of dexamethasone, HGF, and oncostatin M.

Preferably, the mammal-derived ES cell is an ES cell derived from a mouse, a monkey, or a human.

Another aspect of the present invention provides a liver cell obtained by induction of differentiation from an ES cell, which is obtained by the method according to the aforementioned present invention.

Furthermore, another aspect of the present invention provides a method for obtaining a liver cell obtained by induction of differentiation from an ES cell, which comprises a step of inducing the differentiation of a liver cell from an ES cell by the aforementioned method according to the present invention, and a step of separating the differentiation-induced liver cell by flow cytometry (FACS) using fluorescence labeling.

Furthermore, another aspect of the present invention provides a method for screening for a substance capable of promoting or inhibiting the induction of the differentiation of an ES cell into a liver cell, wherein, when a mammal-derived ES cell is induced to differentiate into a liver cell by culturing, in the presence of an M15 cell, the ES cell in the presence of activin and bFGF and then culturing the ES cell in the presence of dexamethasone, HGF, and oncostatin M, the ES cell is cultured in the presence of a test substance, and the level of induction of the differentiation into a liver cell in a case of culturing ES cells in the absence of the test substance is then compared with the level of induction of the differentiation into a liver cell in a case of culturing the ES cells in the presence of the test substance.

Preferably, the test substance is a growth factor or a low molecular weight compound.

Preferably, the level of induction of the differentiation into a liver cell is measured using the expression level of a marker that is expressed in the liver cell as an indicator.

Preferably, the mammal-derived ES cell is an ES cell derived from a mouse, a monkey, or a human.

Furthermore, another aspect of the present invention provides a method for testing liver toxicity, which comprises administering a test substance to the liver cell obtained by induction of differentiation from the ES cell, which is obtained by the aforementioned method according to the present invention, and then analyzing the influence of the test substance on the liver cell.

Furthermore, another aspect of the present invention provides a method for testing drug metabolism, which comprises administering a test substance to the liver cell obtained by induction of differentiation from the ES cell, which is obtained by the aforementioned method according to the present invention, and then analyzing the metabolism of the test substance.

EFFECTS OF THE INVENTION

According to the method of the present invention, an ES cell can be efficiently induced to differentiate into a liver cell. In addition, the effects of an unknown substance to induce the differentiation of an ES cell into the liver can be measured with good sensitivity by applying the culture method of the present invention. Thus, it can be applied as a method for screening for a substance capable of inducing the differentiation into a liver cell.

BEST MODE FOR CARRYING OUT THE INVENTION

The embodiments of the present invention will be described more in detail below. The present invention relates to a method for inducing the differentiation of an ES cell into a liver cell, which is characterized in that it comprises, in the presence of an M15 cell, culturing a mammal-derived ES cell in the presence of activin and bFGF, and then culturing the ES cell in the presence of dexamethasone, HGF, and oncostatin M.

As described above, the present invention relates to induction of the differentiation of a liver cell-like cell from an ES cell. As a result of the analysis of an ES cell-derived liver cell, it was found that the ES cell-derived liver cell is similar to a mature liver cell in the point that the aforementioned cell stores glycogen and expresses a molecular marker such as albumin, a bile acid transporter, or cytochrome P450 metabolic enzyme.

The type of the ES cell used in the present invention is not particularly limited, as long as it is an ES cell derived from a mammal. For example, an ES cell derived from a mouse, a monkey, or a human may be used. As such ES cell, in order to facilitate confirmation of the level of the differentiation of the cell, a cell in which a reporter gene has been introduced in the locus of Pdx1 gene, may be used, for example. For instance, there may be used an ES cell SK7 strain having a GFP reporter transgene under the control of a Pdx1 promoter, which will be used in the after-mentioned examples. Otherwise, there may also be used an ES cell PH3 strain having an mRFP 1 reporter transgene under the control of an Hnf3β endoderm-specific enhancer fragment and a GFP reporter transgene under the control of a Pdx1 promoter.

The mammal-derived ES cell may be cultured by an ordinary method. For example, the ES cells can be maintained on mouse embryonic fibroblasts (MEF), using a Glasgow minimum essential medium (Invitrogen) supplemented with 1,000 units/mL leukemia inhibitory factor (Chemicon), 15% KSR (knockout serum replacement; Gibco), 1% fetal bovine serum (FBS; Hyclone), 100 μM nonessential amino acid (Invitrogen), 2 mM L-glutamine (Invitrogen), 1 mM sodium pyruvate (Invitrogen), 50 units/mL penicillin, 50 μg/mL streptomycin (Invitrogen), and 100 μM β-mercaptoethanol.

In the present invention, ES cells are cultured in the presence of M15 cells acting as supporting cells ; namely, ES cells are co-cultured with M15 cells.

The M15 cell (mouse, mesonephros) used in the present invention has been registered with a cell bank (CAMR Centre for Applied Microbiology & Research (ECACC, Salisbury, Wiltshire)) under registration No. ECACC 95102517. The M15 cell can be obtained in accordance with the descriptions of a publication (Larsson, S. H., Charlieu, J. P., Miyagawa, K., et al. (1995). Subnuclear localization of WT1 in splicing or transcription factor domains is regulated by alternative splicing. *Cell* 81, 391-401). Bank information regarding M15 will be described below.

Version 4.200201
M15 (mouse, mesonephros)
ECACC 95102517
Morphology: Epithelial
Mouse mesonephric epithelium, polyoma virus large T transformed
Depositor: Prof V van Heyningen, MRC Human Genetics Unit, Western General Hospital, Edinburgh, UK (Originator)
No restrictions. Patent: None Specified By Depositor
Properties: Products: WT1 (expressed gene) Applications: Gene expression and protein studies connected to kidney development and Wilms' tumourigenesis.
Available in the following LABORATORY:
CAMR Centre for Applied Microbiology & Research (ECACC, Salisbury, Wiltshire)
DMEM+2 mM Glutamine+10% Fetal Bovine Serum (FBS). Split confluent cultures 1:5 to 1:10 i.e. seeding at 5×1,000 to 1×10,000 cells/cm² using 0.25% trypsin or trypsin/EDTA; 5% CO$_2$; 37° C. [cell growth impaired at lower densities]. Karyotype: Hyperdiploid
Hazard: CZ-II
The WT1-expressing mesonephric cell line M15 (alias Meso 15) was established from mouse mesonephros transgenically expressing the large T protein of polyoma virus under the control of the early viral enhancer. As a tumor suppresser gene with a key role in urogenital development, WT1 is implicated as predisposition gene in the pathogenesis of Wilms' tumor (WT).

Further information
Research council deposit: Yes
Price_code: C
Bibliographic references:
Cell 1995; 81: 391
By Beatrice . . .
TITLE: M15
DATE: 2005/04/24 00:32
URL: http://www.biotechist.unige.it/cldb/c13312.html
European Collection of Cell Cultures,
Health Protection Agency, Porton Down, Salisbury, Wiltshire, UK
June Poulton
European Collection of Cell Cultures
Health Protection Agency,
Porton Down
SP40JG Salisbury, Wiltshire UK
Phone: +44-1980-612512
Fax: +44-1980-611315
E-mail: ecacc@hpa.org.uk
URL: http://www.ecacc.org.uk/

M15 cells can be cultured by an ordinary method using a common medium used for animal cells (for example, an RPMI medium, a DMEM medium, etc.), to which serum and the like are supplemented.

A method for culturing a mammal-derived ES cell in the presence of an M15 cell is not particularly limited. For example, the ES cell can be cultured using an M15 cell as a feeder cell. For example, an undifferentiated ES cell is dissociated with trypsin, and it is then subjected to a suspension culture in a differentiation medium on an untreated culture dish in the absence of LIF, so as to form an embryoidbody. The embryoidbody, which has differentiated for 2 days, is treated with trypsin, and it is then inoculated in a differentiation medium on a plate that has previously been coated (pre-coated) with a single layer of the feeder cell (M15 cell). Thereafter, it is cultured for several days, so that the ES cell can be induced to differentiate into a liver cell.

In the differentiation induction method of the present invention, when ES cells are cultured in the presence of M15 cells, the ES cells are cultured in the presence of activin and bFGF, and thereafter, the cells are cultured in the presence of dexamethasone, HGF, and oncostatin M. In addition, when mammal-derived ES cells are cultured in the presence of M15 cells, BMP4 is also preferably added. By such culture, ES cells can be induced to differentiate into hepatocytes. The differentiation of ES cells into hepatocytes can be confirmed by measuring the expression level of a marker specific to the hepatocytes. As a marker specific to hepatocytes, albumin, a bile acid transporter, or cytochrome P450 metabolic enzyme may be used, for example.

Moreover, according to the present invention, there is provided a method for screening for a substance capable of promoting or inhibiting the induction of the differentiation of an ES cell into a liver cell, wherein, when a mammal-derived ES cell is induced to differentiate into a liver cell by culturing, in the presence of an M15 cell, the ES cell in the presence of activin and bFGF and then culturing it in the presence of dexamethasone, HGF, and oncostatin M, the ES cell is cultured in the presence of a test substance, and the level of induction of the differentiation into a liver cell in a case of culturing ES cells in the absence of the test substance is then compared with the level of induction of the differentiation into a liver cell in a case of culturing the ES cells in the presence of the test substance. As a test substance, a growth factor, a low molecular weight compound, or the like may be used. In this method, the level of induction of the differentiation into a liver cell can be measured using the expression level of a marker that is expressed in the liver cell as an indicator.

Furthermore, according to the present invention, a test substance is administered to the liver cell obtained by induction of differentiation from the ES cell, which is obtained by the method of the present invention, and the influence of the test substance on the liver cell is then analyzed, so that liver toxicity can be tested. Otherwise, a test substance is administered to the liver cell obtained by induction of differentiation from the ES cell, which is obtained by the method of the present invention, and the metabolism of the test substance is then analyzed, so that drug metabolism can be tested.

The present invention will be more specifically described in the following examples. However, these examples are not intended to limit the scope of the present invention.

Examples

Example 1

(A) Materials and Methods
(1) ES Cells

A previously reported SK7 cell line (mouse ES cells) having a Pdx1 promoter-derived GFP reporter-introduced gene was used (International Publication WO2006/126574). The SK7 ES cells were maintained on mouse embryonic fibroblasts (MEF), using a Glasgow minimum essential medium (Invitrogen) supplemented with 1,000 units/mL leukemia inhibitory factor (Chemicon), 15% KSR (knockout serum replacement; Gibco), 1% fetal bovine serum (FBS ; Hyclone), 100 μM nonessential amino acid (Invitrogen), 2 mM L-glutamine (Invitrogen), 1 mM sodium pyruvate (Invitrogen), 50 units/mL penicillin, 50 μg/mL streptomycin (Invitrogen) and 100 μM β-mercaptoethanol.

Human ES cells (KhES-1) (Suemori, H., et al. (2006) *Biochem Biophys Res Commun* 345, 926-32.) were furnished from Dr. Nakatsuji and Dr. Suemori (Kyoto University), and were used in accordance with the hES cell guidelines of the government of Japan. Undifferentiated hES cells were maintained on an MEF feeder layer inactivated with 10 μg/mL mitomycin C, under 3% $CO_2$, using DMEM/F12 (Sigma) containing 20% KSR, 2 mM L-glutamine, 100 μM nonessential amino acid, and 100 μM β-mercaptoethanol. For the subculture of the hES cells, the hES cell colonies were separated from the supporting cell layer by treating the cells with 0.25% trypsin and 0.1 mg/mL collagenase IV at 37° C. for 5 minutes in PBS containing 20% KSR and 1 mM $CaCl_2$. Thereafter, a culture solution was added to the colonies, and suction was gently carried out using a pipette several times, so as to divide the ES cell mass into small sections (5-20 cells). The subculture was carried out at a division ratio of 1:2.

(2) Supporting Cells

Mouse fetal kidney-derived M15 cells (Larsson, S. H., et al. (1995). Cell 81, 391-401) were furnished from Dr. Nose (Mitsubishi Kagaku Institute of Life Sciences, Tokyo) and Dr. M. Rassoulzadegan (University of Nice-Sophia Antipolis, France). The M15 cells were cultured in DMEM containing 10% FBS. Before use, the M15 cells were treated with 10 μg/mL mitomycin C (Sigma) for 2.5 hours. The M15 cells ($8 \times 10^5$ or $2 \times 10^5$ cells per well) were inoculated on a 6-well or 24-well plate coated with gelatin. Thereafter, the ES cells were placed on the supporting cells in a state in which the M15 cells became confluent (3) Differentiation of ES cells For use in differentiation studies, mouse ES cells were transferred onto a gelatin-coated plate that did not contain MEF, and the cells were then cultured for 2 days to eliminate MEF. Thereafter, the ES cells (the number of cells: 5,000 and 20,000, respectively) were inoculated on a 24-well or 6-well plate (Nunc) that had previously been coated with the M15 cells. Subsequently, using DMEM containing 100 μM nonessential amino acid, 2 mM L-glutamine, 50 units/mL penicillin, 50 μg/mL streptomycin and 100 μM β-mercaptoethanol, the cells were cultured in a differentiation culture solution containing 10% FBS and 4,500 mg/L glucose from the initial day of culture (d0) to day 4 (d4), and after d4, the cells were then cultured in another culture solution containing 10% KSR and 2,000 mg/L glucose. Thus, the cells were cultured for a maximum of 30 days. In order to induce the terminally differentiated endoderm, activin A (20 ng/mL) and bFGF (50 ng/mL) were added during the period from d0 to d4. Moreover, HGF (10 ng/mL) and dexamethasone (1 μM) were added during the period from d4 to d30. The culture solution was replaced with a fresh one containing a growth factor every two days. The details of such growth factor will be described at the end of the diferentiation section.

With regard to human ES cells, KhES-1 cells (20,000 and 80,000 cells per well, respectively) were inoculated on a 24-well plate and a 6-well plate on which M15 cells had previously been cultured. The ES cells were cultured for a maximum of 40 days in a differentiation culture solution (DMEM containing 10% KSR, 4,500 mg/L glucose, 100 μM nonessential amino acid, 2 mM L-glutamine, 50 units/mL penicillin, 50 μg/mL streptomycin, and 100 μM β-mercaptoethanol). From d0 to d10, activin A (20 ng/mL) was added in order to induce the terminally differentiated endoderm. From d10 to d40, HGF (10 ng/mL), Dex (1 μM), and oncostatin M (10 ng/mL) were added in order to induce differentiation into the liver. The culture solution was replaced with a fresh one containing a growth factor every two days. The growth factor will be described in (4) below. For a precise schedule including the addition of each growth factor, please refer to each figure.

(4) Growth Factors and Inhibitory Factors

The following concentrations were applied.

Recombinant human activin A (R&D Systems): 20 ng/mL; recombinant human bFGF (Peprotech): 50 ng/mL; recombinant human BMP4 (R&D Systems): 50 ng/mL; SU5402 (Mohammadi, et al., (1997). Science 276, 955-60.) (Calbiochem): 10 μM; recombinant mouse Noggin/Fc Chimera (R&D Systems): 100 ng/mL; recombinant human hepatic cell growth factor (HGF, Peprotech): 10 ng/mL; dexamethasone (Dex, Sigma): 1 μM; recombinant human oncostatin M (OSM, Sigma): 10 ng/mL.

(5) Flow Cytometry Analysis

Cells were dissociated with Cell Dissociation Buffer (Invitrogen) at 37° C. for 20 minutes. As an antibody, either a biotin-labeled anti-E-cadherin monoclonal antibody (mAb) ECCD2 (Shirayoshi, Y, et al., (1986). Cell Struct Funct 11, 245-52.) or a phycoerythrin (PE)-labeled anti-Cxcr4 mAb 2B11 (BD Biosciences Pharmingen) was used. The stained cells were filtrated with a 40-μm mesh, and were then re-suspended in a solution prepared by adding a propidium iodide to a Hank's buffered salt solution (Sigma) containing 1% bovine serum albumin. The re-suspension was analyzed with FACS Canto (Becton Dickinson) or was sorted with FACS Aria (Becton Dickinson). The data was recorded by a BD FACSDiva software program (Becton Dickinson), and was then analyzed by a Flowjo program (Tree Star).

(6) Real-Time PCR Analysis

RNA was extracted from the ES cells using RNeasy mini-kit (Qiagen), and it was then treated with DNase (Qiagen). In order to examine an RT reaction, 3 μg of RNA was subjected to reverse transcription using MMLV reverse transcriptase (Toyobo Co., Ltd.) and oligo dT primers (Toyobo Co., Ltd.). 1 μL of 5-times diluted cDNA (1% of an RT product) was used in PCR analysis. The primer sequences of each primer set are shown in Table 1. The expression level of mRNA was quantified using SyberGreen of ABI 7500 thermal cycler (Applied Biosystems). The expression level of each gene was standardized with the expression level of β-actin. PCR conditions were as follows. An operation consisting of denaturation at 95° C. for 15 seconds and annealing and elongation at 60° C. for 60 seconds was repeated for 40 cycles. The β-actin level was standardized among samples by subtracting a mean β-actin Ct value from the Ct value of each gene (Ct value: the number of cycles at which PCR amplification products reached a certain amount). Each target mRNA level was indicated with arbitrary unit, and it was determined by a standard curve method. Using SyberGreen detection, an amplification product was confirmed on 5% nondenaturing polyacrylamide gel by electrophoresis, and it was then stained with SYBR Green I (Molecular Probes). The predicted size of the amplification product matched with the size calculated by visual examination.

TABLE 1

Table 1. PCR primers (SEQ ID NOS 1-24, respectively, in order of appearance) used to detect mouse gene expression

| Gene | Forward primer | Reverse primer |
| --- | --- | --- |
| Abcb11 (Bsep) | GAGTGGTGGACAGAAGCAAA | TGAGGTAGCCATGTCCAGAA |
| Afp | TCGTATTCCAACAGGAGG | AGGCTTTTGCTTCACCAG |
| Alb1 | CTTAAACCGATGGGCGATCT-CACT | CCCCACTAGCCTCTGGCAAAAT |
| B-actin | GTGATGGTGGGAATGGGTCA | TTTGATGTCACGCACGATTTCC |
| Cyp2b10 | GCCCAATGTTTAGTGGAGGA | GACTTCTCCTTCTCCATGCG |
| Cyp3a11 | ATAGAGCTTTGCTGTCCCCC | CGGCTTTCCTTCATTCTGTC |
| Cyp3a13 | CCCTGCTGTCTCCAACCTT | TGCGATTCTCTTTCATTCGTT |
| Krt19 | GTCCTACAGATTGACAATGC | CACGCTCTGGATCTGTGACAG |
| Shh | GGAACTCACCCCCAATTACA | GAAGGTGAGGAAGTCGCTGT |

TABLE 1-continued

Table 1. PCR primers (SEQ ID NOS 1-24, respectively, in order of appearance) used to detect mouse gene expression

| Gene | Forward primer | Reverse primer |
| --- | --- | --- |
| Slco1a4 (Oatp2) | GACGGCTCAGTGTTCATTC | CTTCTAGCTGGTCCCTCTT |
| Sult2a1 | GGAAGGACCACGACTCATAAC | GATTCTTCACAAGGTTTGTGTTACC |
| Ugt1a1 | TCTGAGCCCTGCATCTATCTG | CCCCAGAGGCGTTGACATA |

ABcb11, ATP-binding cassette sub-family 8 member 11; Afp, a-fetoprotein; Alb1, albumin1; Krt19, cytokeratin 19; Shh, sonic hedgehog; Sult2a1, sulfotransftrase family 2A dehydroeplandrosterone-preferring member 1; Ugt1a1, UDP glucuronosyltransferase 1 family polypeptide A1

(7) Immunocytochemistry

For whole mount immunocytochemical analysis, ES cells were inoculated on 24-well Thennanox coverslips (Nunc). Using TCS-SP2 Spectral Confocal Scanning System (Leica), a confocal image was obtained. Using IX 71 Inverted (Olympus), a phase-contrast image was obtained. The following antibodies were used in detection: mouse anti-GFP (Roche), rabbit anti-α-fetoprotein (AFP, Biomeda), goat anti-albumin (Sigma), fluorescein isothiocyanate (FITC)-labeled *Dolichos biflorus* agglutinin (DBA) lectin (Sigma), rabbit anti-α-1-anti-trypsin (Sigma), rabbit anti-CYP3A2 (Biomol), rabbit anti-CYP7A1 (Santa Cruz), and mouse anti-Oct3/4 (Santa Cruz). As secondary antibodies, an Alexa568-labeled goat anti-rabbit antibody, donkey anti-goat antibody (Molecular Probes), and an Alexa488-labeled goat anti-mouse antibody, goat anti-rabbit antibody, and donkey anti-goat antibody (Molecular Probes) were used. The cells were subjected to counterstaining using DAPI (Roche). In order to quantify the number of the Afp-expressing cells of FIG. 3B, the region of an Afp-positive stained image was analyzed using Lumina Vision program (Mitani Corporation).

(8) Periodic Acid-Schiff (PAS) Staining Analysis

In order to examine the presence or absence of the generation and storage of glucose by the cultured cells as an indicator of functional maturation, PAS staining was carried out. The cultured cells were treated with 3.3% formalin for 10 minutes, and intracellular glucose was then stained with a PAS staining solution (Muto Pure Chemicals Co., Ltd.). Staining was carried out in accordance with the instructions of the manufacturer.

(B) Results (1) Mesoderm-Derived M15 Cells Directed ES Cells to Differentiate into hepatic Endodermal Cells.

As previously reported, it is considered that a co-culture method using mesoderm-derived M15 cells can be replaced with embryonic materials, and that the M15 cells cause ES cells to region-specifically differentiate into the endodermal tissues of the lung, liver, pancreas, bowel, and the like. As a result of time series analysis, it became clear that ES cells differentiate into an endoderm lineage via multiple processes. As a result of using the method of the present inventors, ES cells successively differentiated in vitro into a mesendoderm, a definitive endoderm, and finally, a region-specifically terminally differentiated endoderm-derived organ. This recapitulates the in vivo induction processes of early embryonic development.

The pancreas and the liver develop from a portion adjacent to the foregut ventral endoderm of an embryo during the development process. It has been reported to date that there exist precursor cells common in the pancreas and the liver, and that signals from the cardiac mesoderm specify differentiation into the pancreas and the liver. According to this model, such a signal as FGF is transmitted from the cardiac mesoderm, and the fate of the cells was directed to the liver. In the present invention, culture conditions under which the differentiation of the cells into the liver, but not into the pancreas, preferentially occurs were analyzed. There were used ES cells SK7 (International Publication WO2006/126574) derived from a transgenic mouse P#48.9 (Gu, G., et al., (2004). *Development* 131, 165-79.) in which a green fluorescent protein (GFP) reporter had been expressed using a Pdx1 promoter. According to the recent studies by the present inventors, it was revealed that activin and bFGF promote the development of the mesendoderm and terminally differentiated endoderm from ES cells. Thus, in the present invention, activin and bFGF were added during the initial 4 days of culture differentiation. Thereafter, from the day 4 (d4) to day 8 (d8), the ES cells were cultured in FBS containing various soluble factors and having a different glucose concentration (2,000 mg/L or 4,500 mg(L). On the 8$^{th}$ day, the ratio of the terminally differentiated endoderm defined as E-cadherin+/Cxcr4+ and the ratio of Pdx 1-expressing cells determined by flow cytometry analysis were evaluated (Yasunaga, M., et al., (2005). *Nat Biotechnol* 23, 1542-50.). FIG. 1A shows that the ratio of endodermal cells and Pdx1-expressing cells was increased by the addition of activin and bFGF.

In addition, the effects obtained by adding dexamethasone (Dex), a hepatic cell growth factor (HGF), and oncostatin M (OsM) after termination of the addition of activin and bFGF were examined. The ratio of the Pdx1-expressing cells was further decreased by the addition of Dex, HGF, and OsM (FIG. 1A).

In order to analyze the range of differentiation of the terminally differentiated endoderm into the liver, the transcript amounts of sonic hedgehog (Shh) and α-fetoprotein (Afp) acting as an initial liver marker were measured by real-time PCR (FIG. 1B). The terminally differentiated endodermal (E-cadherin+/Cxcr4+) cells were separated by flow cytometry. Using the terminally differentiated endodermal cell-derived cDNA as a template, a real-time PCR analysis was carried out In the case of using FBS, Afp transcription was hardly induced. Under KSR conditions, Afp transcription was increased. Further, in a case in which Dex, HGF, and OsM were added from d4 to d8 under low glucose conditions, the number of Afp-expressing terminally differentiated endodermal cells became largest, the number of Pdx1/GFP-positive cells was increased (FIG. 1A, black), and Shh or Afp transcription was decreased (FIG. 1B, black). In contrast, when Dex, HGF, and OsM were added, differentiation into the liver occurred preferentially, and as a result, the number of the Pdx1/GFP-positive cells was decreased (FIG. 1A, gray), and Shh or Afp transcription was increased (FIG. 1B, gray).

As a result of the immunohistochemical analysis, it was confirmed that the Pdx1-expressing cells and the AFP-expressing cells were complementary, and that almost all the cells were generated from different colonies (FIG. 2A). When activin and FGF were continuously added, the Pdex1-expressing cells appeared preferentially (activin & bFGF columns). When the addition of these two factors was terminated, FBS was replaced with KSR, and Dex, HGF, and OsM were then added to the culture solution having a glucose concentration of 2,000 mg/L (2,000 KsR, Dex & HGF & OsM), the number of the Pdx1-expressing cells was decreased, and the number of the AFP-expressing cells was increased to a considerable extent.

The combination of Dex, HGF, and OsM was considered to support the differentiation of ES cells into the liver. Thus, KSR was used at a glucose concentration of 2,000 mg/L, and a comparison was made between culture conditions involving the addition of one factor or two factors. FIG. 2B shows that AFP expression was promoted in the order of Dex>HGF>OsM. When two factors were added, in the combination of Dex and HGF, the differentiation of the AFP-expressing cells from the ES cells occurred most frequently, and the differentiation of the Pdx1-expressing cells occurred least frequently (FIG. 2B). Likewise, in the assay carried out at d30, albumin (Alb)-expressing cells were observed most frequently (FIG. 2C). Considering the obtained results, from d0 to d4, activin and bFGF were added to the culture solution in FBS having a glucose concentration of 4,500 mg/L. From d4, FBS was replaced with KSR, and the cells were then cultured in a culture solution with a low glucose concentration (2,000 mg/L), to which Dex and HGF had been added. Thus, a more detailed analysis was carried out under the aforementioned conditions.

Figure 3:
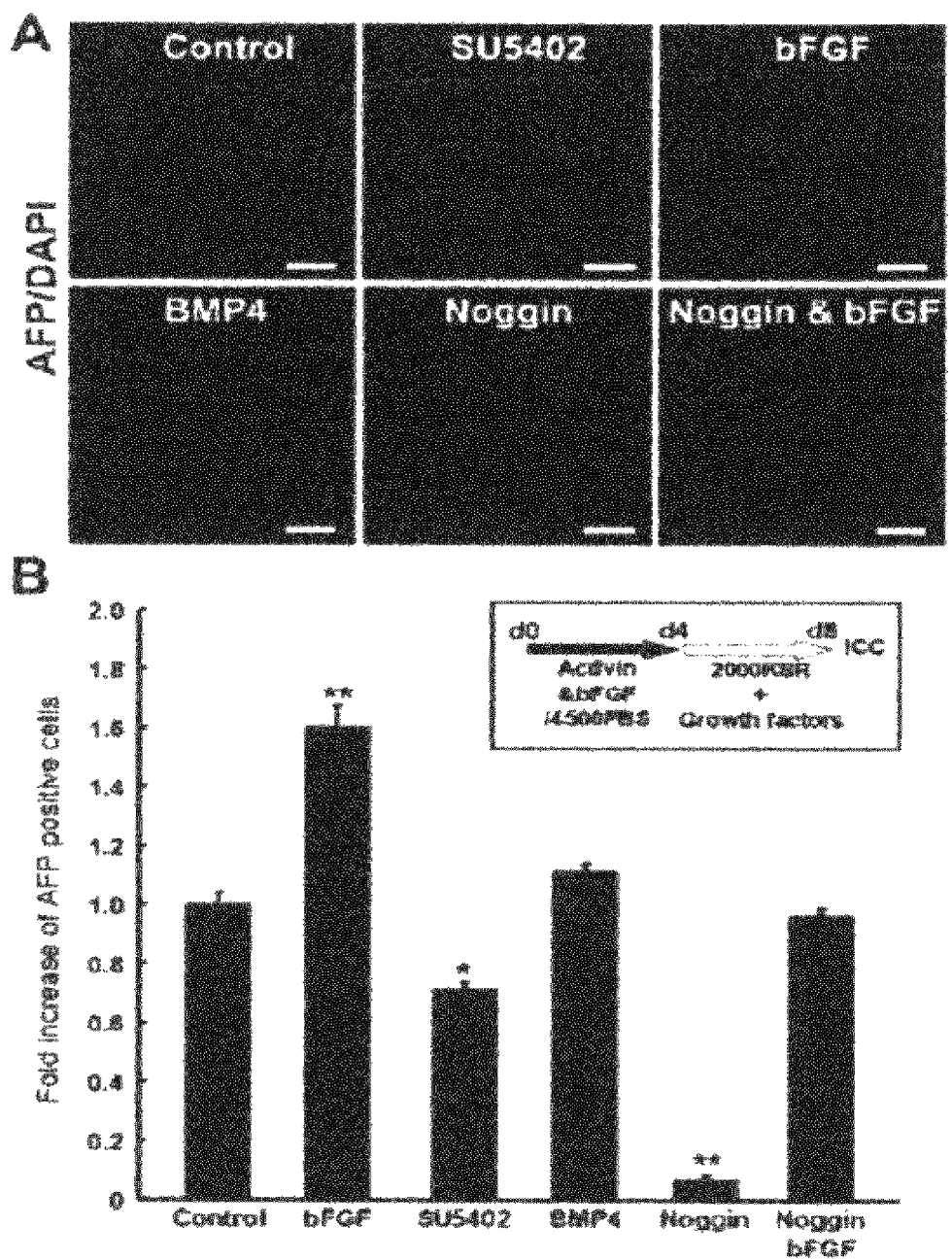
FIG. 3 shows that BMP signaling and FGF signaling are essential for differentiation from the ES cell-derived, terminally differentiated endoderm into liver cells. ES cells were cultured together with activin and bFGF in a culture solution containing activin, bFGF, 10% FBS, and 4,500 mg/L glucose from d0 to d4. Thereafter, the culture solution was replaced with another culture solution containing 10% KSR and 2,000 mg/L glucose. Then, the instructed growth factors were supplemented, or no such growth factors were supplemented, and the cells were continuously cultured. In the immunohistochemical analysis shown in FIG. 3(A), a nucleus was subjected to counterstaining with an anti-AFP antibody and DAPI. When Noggin was added, differentiation of the cells into AFP-positive cells was inhibited. On the other hand, when bFGF was added, the inhibitory action of Noggin was compensated. The bar indicates 200μm. Regarding FIG. 3(B), in comparison with a control, AFP-positive cells multiplicatively increased. The AFP-positive site in each fluorescent image was analyzed by Lumina Vision program. The numerical value as a result was indicated by a mean value ±standard error (n =3). *p <0.05 and **p <0.01 vs. control (Student's t-test).

(2) BMP and FGF Signals are Extremely Important for Differentiation of Endoderm Terminally Differentiated from ES Cells into Liver In the present invention, using BMP4, bFGF, and their antagonists Noggin and SU5402, the effects of these substances on differentiation into the liver were analyzed (FIG. 3). When only FGF was added, the number of AFP-positive cells was increased. When SU5402 acting as an inhibitory factor of FGF receptor I was added, the number of AFP-positive cells was decreased. When Noggin was added, almost all AFP-expressing cells disappeared. However, when bFGF was added, such AFP-expressing cells were recovered. From these results, it became clear that BMP signaling is necessary for differentiation into the liver, and that FGF signaling enhances the effects of BMP.

(3) It became clear from a temporal analysis that sequential expression of molecular markers shows differentiation into hepatoblasts and then differentiation into hepatocytes and bile duct cells.

Figure 4:
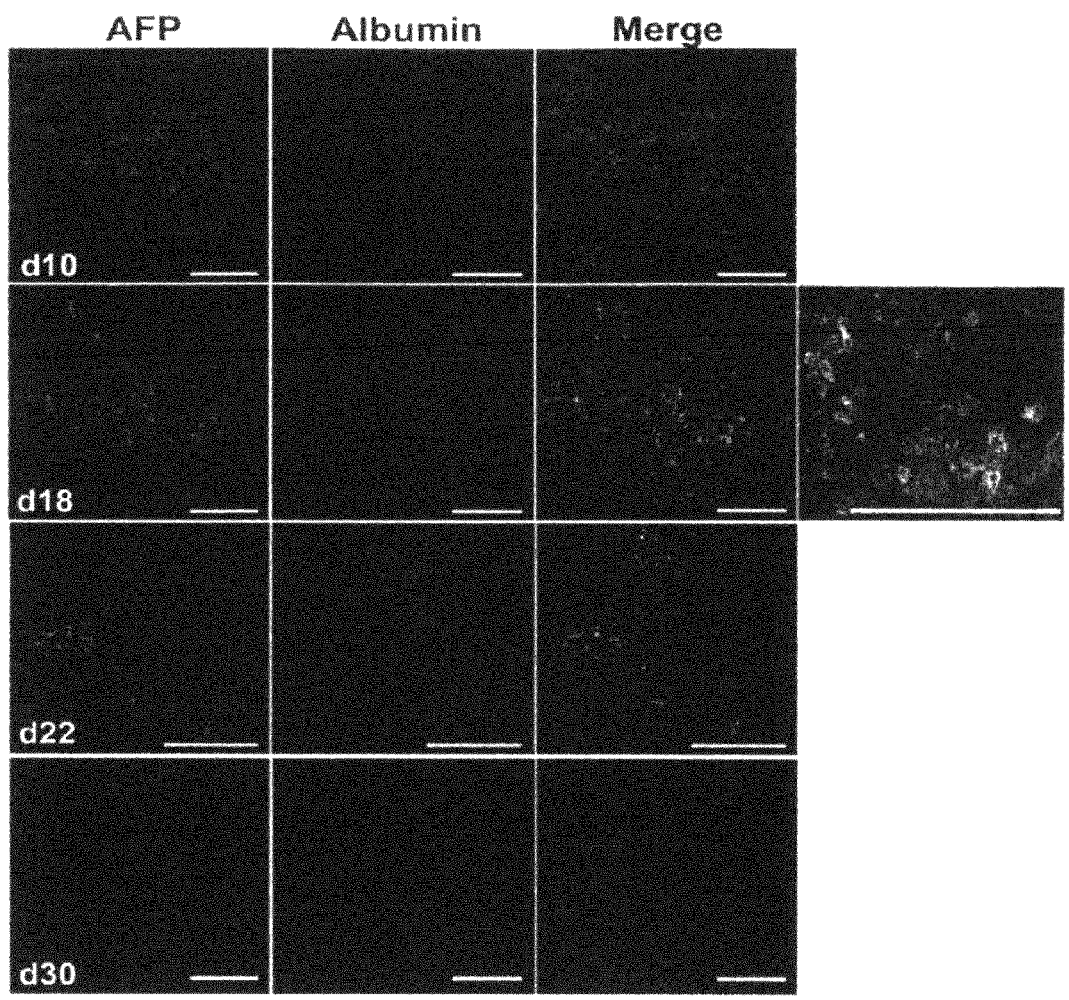
FIG. 4 shows that it became clear from the time-series analysis that AFP-positive cells and albumin-positive cells were successively induced. ES cells were cultured from d0 to d4in a culture solution containing activin, bFGF, 10% FBS, and 4,500 mg/L glucose. From d4 to d8, the culture solution was replaced with another culture solution containing Dex, HGF, 10% KSR, and 2,000 mg/L glucose. The differentiated ES cells were stained with AFP (green) and Alb (red) on d10, d18, d22, and d30. On d10, AFP +liver precursor cell-like cells were generated (d10, green). On d18, AFP+/Alb+cells were generated (d18, yellow). On d22, AFP+/Alb+hepatoblasts increased (d22, red), and AFP+cells decreased (d22, green). On d30, almost all the AFP+cells disappeared, and albumin+cells formed a clear colony. The bar indicates 200 μm.

In the present example, the temporal expression of mature hepatic molecular markers was analyzed. AFP- or Alb-expressing cells were analyzed by an immunohistochemical analysis (FIG. 4). The culture was extended up to a maximum of 30 days. FIG. 4 shows that AFP-positive cells first appeared and Alb-positive cells were then detected on d18. At this time point, cells co-expressed AFP and albumin existed. Thereafter, AFP-expressing cells decreased, and Alb-expressing cells increased. Thus, such results suggested that hepatocytes derived from ES cells first formed immature liver cell precursor cells (AFP+/Alb−), and thereafter, such liver cell precursor cells differentiated into hepatocyte (AFP−/Alb+) via the stage of hepatoblast cells (AFP+/Alb+).

Hepatoblasts are precursor cells having bipotency, which may differentiate into both hepatocyte and bile duct cells. Thus, in the present example, the culture of a bile duct cell lineage was analyzed. As a result of an immunohistochemical analysis, it was demonstrated that hepatocytes were separated from bile duct cells, and that the two types of cells formed Alb+ colonies and *Dolichos biflorus* agglutinin (DBA) lectin+ colonies, respectively (FIG. 5A). On the other hand, as a result of the immunohistochemical analysis of mature molecular markers, it was found that a part of albumin-positive cells simultaneously expressed both mature hepatocyte markers such as α-antitrypsin and cytochrome P450 (Cyp) enzymes, Cyp3A and Cyp7A1 (FIG. 5B). The hepatocyte marker, α-antitrypsin, is an inhibitory factor of serine protease and trypsin. Cyp3A is a drug- and steroid-metabolizing enzyme belonging to a cytochrome P450 subfamily. Cyp7A1 is cholesterol 7α hydroxylase, which adjusts a pathway for converting cholesterol to bile acid. Cyp7A1 is expressed in the liver but is not expressed in yolk sac tissues, and therefore Cyp7A1 is useful as a marker for hepatocytes.

(4) Functional Characteristics of ES Cell-Derived Hepatocytes

Figure 5:
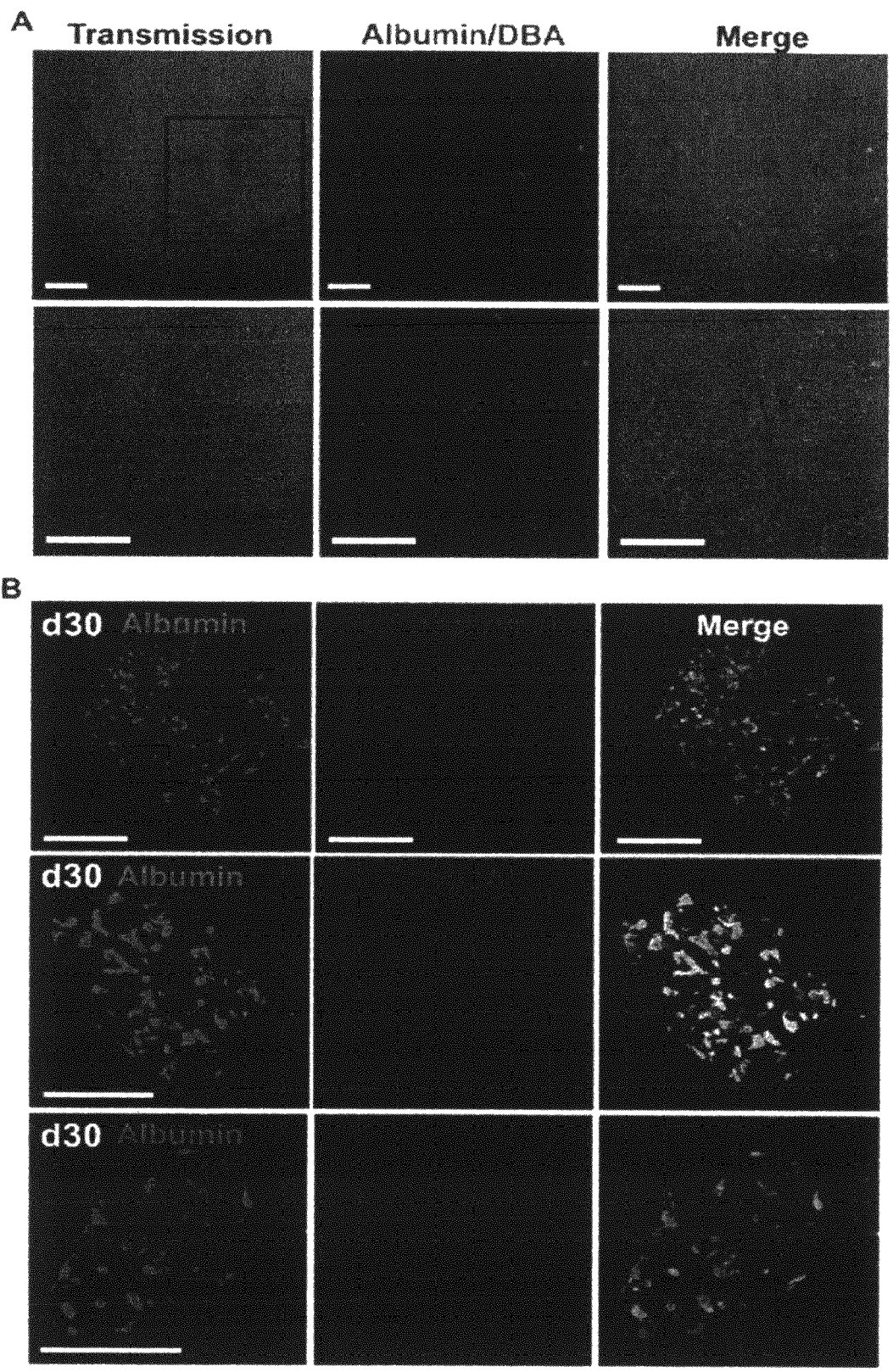
FIG. 5 shows the analysis of the molecular markers of bile duct cells and haptocytes. From d4, ES cells were cultured in a culture solution containing Dex and HGF, which was a condition optimal to liver differentiation. On d30, the differentiated ES cells were stained with Alb (a hepatocyte marker, red) and Dolichos biflorus agglutinin (DBA) lectin (bile duct cell marker, green). It was confirmed that Alb+cells and DBA lectin+cells formed different colonies. Regarding FIG. 5(A), on d30, the differentiated ES cells were stained with Alb (green) and with mature hepatocyte markers, αd-antitrypsin, Cyp3A, and Cr 7A1 (red). The bar indicates 200 μm.
Figure 6:
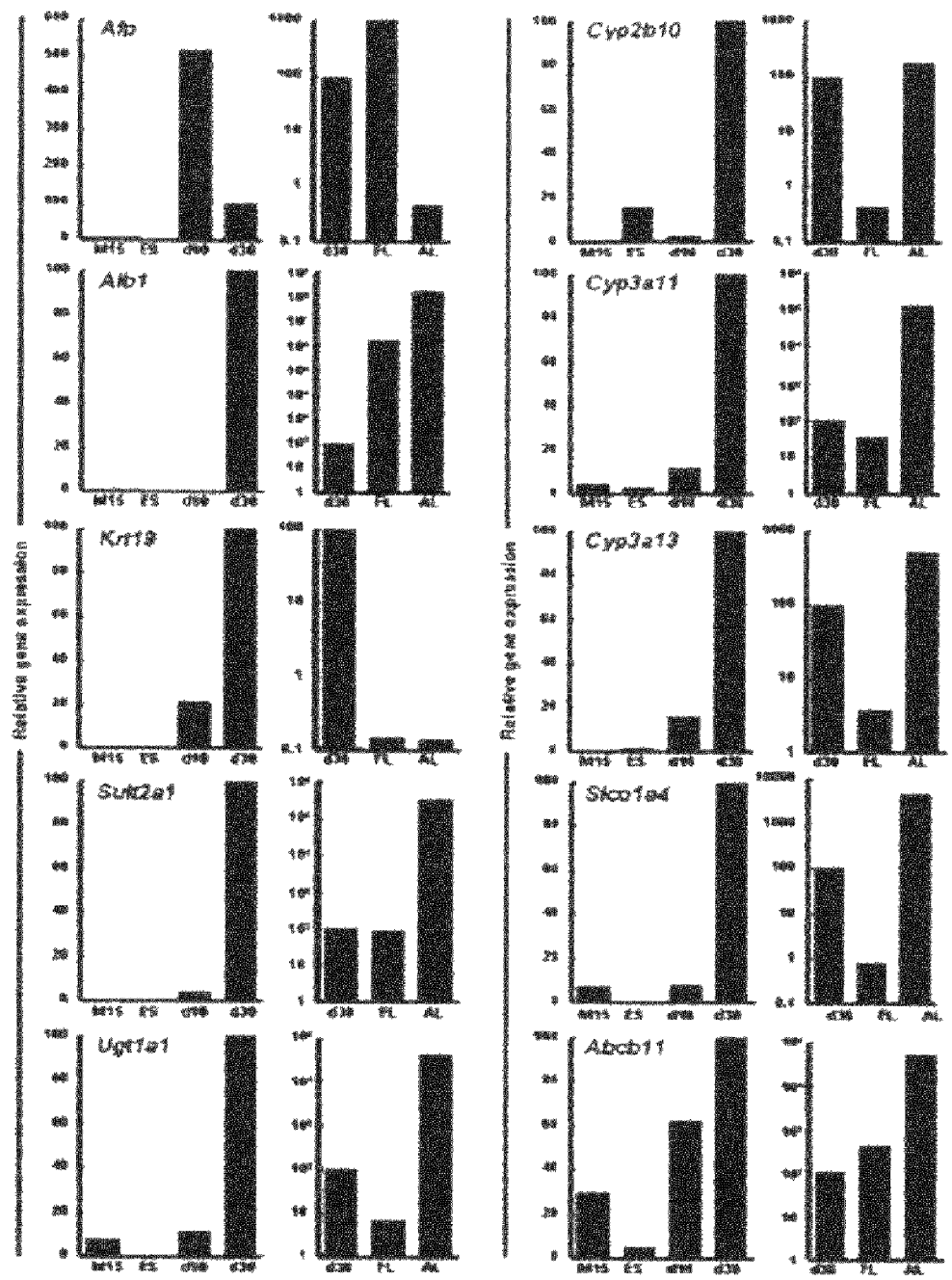
FIG. 6 shows the results obtained by performing a molecular analysis on the liver molecular markers of ES cell-derived hepatic cells by real-time PCR, and then comparing fetal liver-derived hepatic cells with mature liver-derived hepatic cells. The transcription of a hepatic marker gene was quantified by a real-time PCR analysis. The transcription level was normalized with the level of β-actin. Each value was normalized with the level of the differentiated ES cells on d30. The level on d30 was defined as 100, and a relative gene expression level was expressed with a graph. The ES cells were cultured in a culture solution containing Dex and HGF, which was a condition optimal to hepatocyte differentiation. The term "M15" indicates M15 cells; the term "ES" indicates undifferentiated ES cells; the term "d10 and d30" indicates the differentiated ES cells on the 10th and 30th days that were cultured on M15 cells; the term "FL" indicates an E12.5 fetal liver; and the term "AL" indicates an adult liver.

To measure the maturity of the hepatocytes, the molecular analysis of a liver molecular marker was carried out by real-time PCR on day 10 and 30 after the culture, and the results were compared with those of the hepatocytes of E12.5 fetal liver or mature liver. In the differentiated ES cells on day 30, Afp transcription was decreased. This result matched with the aforementioned immunohistochemical data (FIG. 5). The same analysis was carried out using other mature liver cell markers, Alb1, keratin 19 (Krt19), cytochrome P450 enzymes Cyp2b10, Cyp3a11 and Cyp3a13, hydroxysteroidsulfotransferase (Sult2a1), glucuronic acid transferase (Ugt1a1), organic anion transport polypeptide (Slco1a4), and bile salt export pump (Abcd11) (FIG. 6). These mature liver cell markers were detected on d10, and they were then increased to a high level on d30 thereof. The expression level of each marker was compared with that of a fetal liver cell and that of a mature liver cell. As a result, the expression levels of almost all the markers were the same as those of the fetal liver cells. However, Cyp2b10, Cyp3a13, and Slco1a4 exhibited expression levels that were higher than those of the fetal liver cells. These results demonstrated that cells differentiated from ES cells express many mature liver cell markers.

Figure 7:
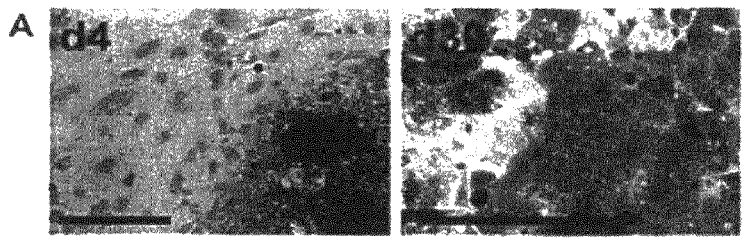
FIG. 7 shows the functional analysis of ES cell-derived hepatocytes. ES cells were cultured in a culture solution containing Dex and HGF, which was a condition optimal to hepatocyte differentiation. Periodic acid-Schiff staining was carried out on the differentiated ES cells on d30. As a result, in multiple colonies, many hepatic cells stored glycogen in the cytoplasm thereof (strong red). This phenomenon was not observed in the differentiated ES cells or M15 cells on d4. An inverted microscope transmission image of ES cell-derived hepatocyte.

Subsequently, the functional characteristics of ES cell-derived hepatic cells were examined. The culture was subjected to periodic acid-Schiff staining. As a result, on d30, cytoplasm was stained red in almost all cells. This result shows the occurrence of glycogen storage, which is characteristic for mature liver cells (FIG. 7).

(5) Application of human ES cells

In order to analyze the applicability of the same culture method to human ES cells, KhES-1 cells were used. As a result of an immunohistochemical analysis, it was found that AFP used as an initial immature liver marker was induced on d20. When Dex, HGF, and OsM were added, AFP-expressing cells increased, and at the same time, undifferentiated ES cells expressing Oct3/4 decreased (FIG. 8A).

Alb-positive colonies were confirmed on d40. In such Alb-positive colonies, DBA lectin-positive cells, which show the presence of bile duct cells, were observed. DBA lectin-positive cells were hardly detected in mouse ES cells (FIG. 8B). The presence of albumin-positive colonies and the presence of DBA lectin-positive colonies proved differentiation of the human ES cells into the heptocytes and the bile duct cells, respectively. These results demonstrated that, as with mouse ES cells, KhES-1 cells also differentiate into both the hepatocytes and the bile duct cells.

(C) Discussion

In the present example, ES cells were cultured on M15 cells used as supporting cells, so that the ES cells could successfully differentiate into hepatic lineages in vitro. Specifically, cell differentiation was successfully induced by adding a growth factor or terminating such addition. The M15 cells used as supporting cells expressed activin and FGF by themselves. However, by adding activin and bFGF from the outside, differentiation of the ES cells into the mesendoderm, the endoderm, and the pancreas were further promoted. That is to say, it was demonstrated that activin and bFGF are essential in the induction process of the differentiation of the ES cells into the mesendoderm, the endoderm, and the pancreas. When an activin or bFGF signaling pathway was inhibited, terminal differentiation into the endoderm was prevented. After d4, the ES cells were cultured under conditions in which activin and bFGF were eliminated. As a result, not differentiation into Pdx1-expresing cells, but differentiation into the hepatic lineage was promoted.

Figure 2:
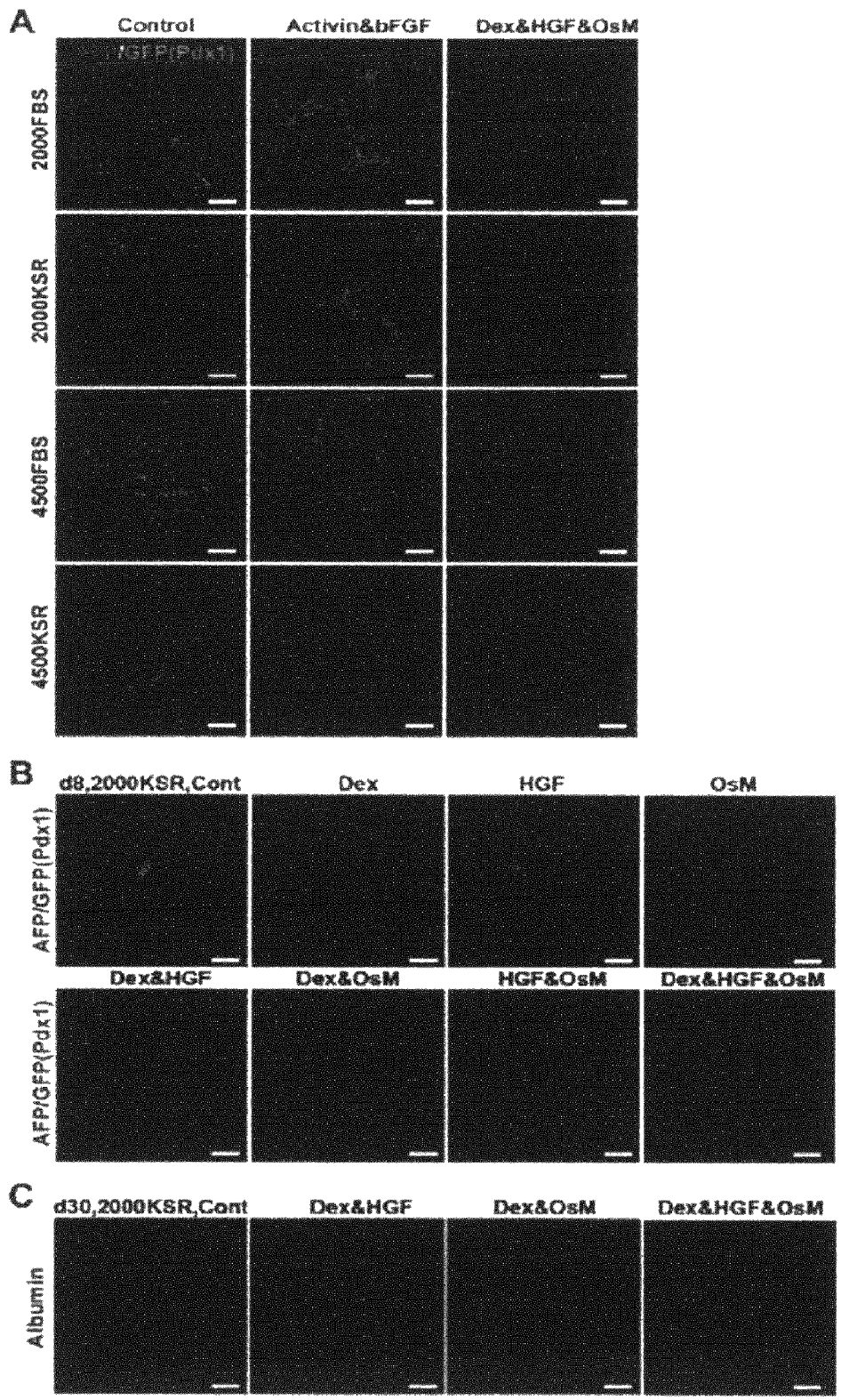
FIG. 2 shows the results obtained by making a comparison among the actions of various factors in the formation of ES cell-derived Pdx//GFP- cells or AFP-expressing cells by an immunohistochemical analysis.

The results of the present example suggested that differentiation into hepatic cells is enhanced under serum-free conditions. The present example demonstrated that the elimination of serum inhibits Pdx1 expression and at the same time, it enhances the induction of hepatic fate very strongly. This result attested the presence of an unknown serum factor for inhibiting differentiation into hepatic cells (FIGS. 1 and 2).

In the present example, BMP, bFGF, and their antagonists Noggin and SU5402 were also examined (FIG. 3). Of these, bFGF increased AFP-expressing cells, and SU5402 decreased them. AFP-expressing cells completely disappeared by Noggin, but AFP-expressing cells were recovered by bFGF. These results made it clear that both BMP4 and bFGF are necessary for differentiation into the hepatic lineages.

Afp synthesis starts immediately after fertilization. It has been reported that Alb1 transcription is detected by RT-PCR at E13.5 in an early case (Petkov, P. M., et al., (2004) *Hepatology* 39, 617-27.). This report matched with the experimental results of the present example (FIG. 4). Dynamic and quantitative PCR analyses demonstrated that Afp expression precedes Alb1 expression. These analyses also suggested that ES cell-derived hepatic cells mimic an ordinary liver developmental program (FIG. 6). Moreover, the analyses also demonstrated that DBA lectin-positive cells differentiate from ES cells. From the aforementioned results, it was demonstrated that a liver cell lineage including bile duct cells and hepatocytes can be induced by the method of the present invention (FIG. 5).

Furthermore, in the present invention, it was also demonstrated that the enzymatic functions of Sult2A, Ugt1A, Cyp2b10, Cyp3a11, Cyp3a13, and the like in detoxification pathways were induced by treatment with Dex and HGF (FIG. 6). Cyp3A4 is related to the metabolism of half or more of currently used drugs. This enzyme is associated with clinically important drug-drug interaction regarding Cyp3A4 inhibition or several cases involving toxicity. A certain drug is able to actively control the activity level of Cyp3A4, and thus it changes the clearance of a combined drug that is a substrate of Cyp3A4. Accordingly, it is considered important to evaluate the ability of a drug for inhibiting Cyp3A4 metabolism in a drug discovery process. Cyp3A11, Cyp3A13, and Cyp3A25 are included in 6 Cyp3A isoforms identified in mouse.

As a result of a gene expression analysis by real-time PCR, it was revealed that ES cell-derived hepatic cells express liver-specific markers and enzyme genes (FIG. 6). A biochemical analysis suggested that hepatic cells derived from ES cells show glycogen storage which is a characteristic of ordinary mature hepatocytes (FIG. 7).

Figure 8:
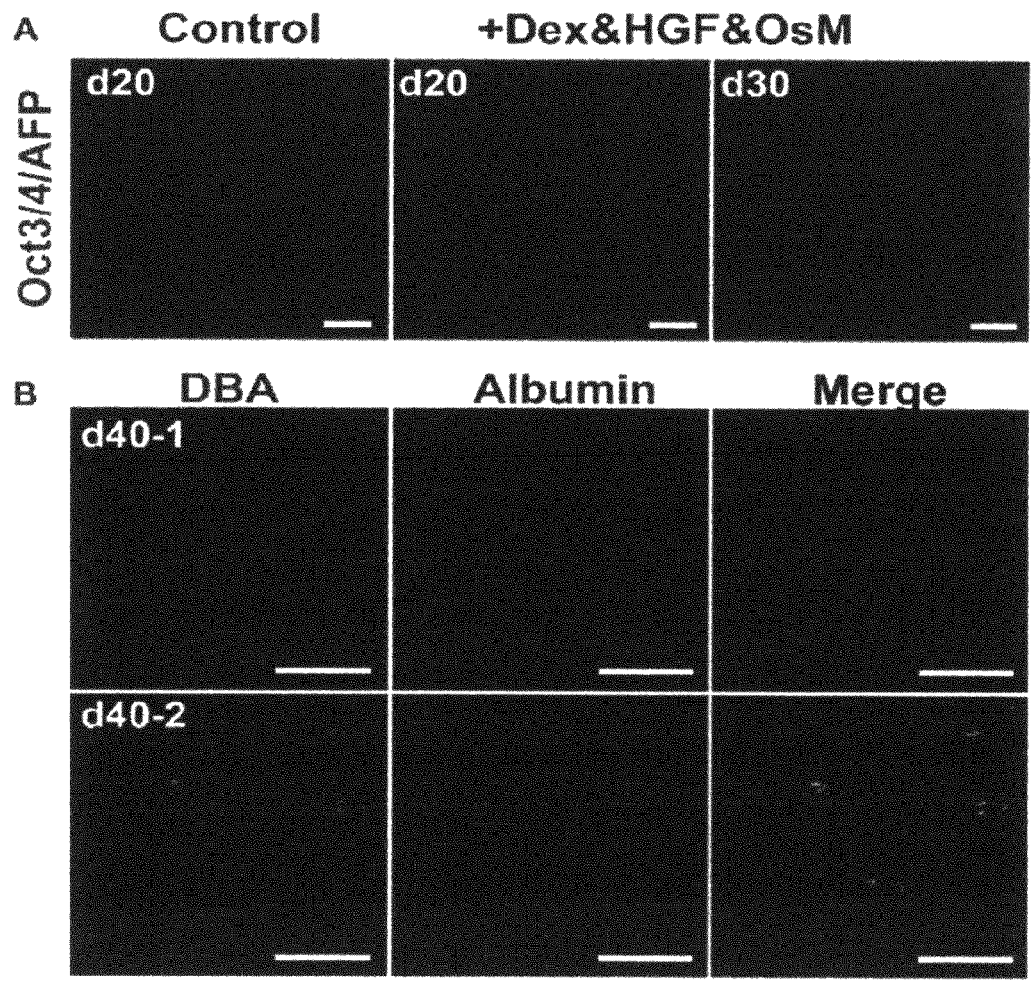
FIG. 8 shows the differentiation of human ES cells into hepatocyte-like cells. The figure shows the differentiated human ES cells (KhES-1) on d10, which were cultured on M15cells, while 20 mg/L activin, 10% KSR, and 4,500 mg/L glucose were added. On d10, the contents of the culture solution were changed to 1 mM Dex, 10 ng/mL HGF, and 10 ng/mL OsM. Regarding FIG. 8(A), on d20 and d30, the differentiated ES cells were stained with AFP (immature hepatic cell marker, red) and Oct3/4 (undifferentiated ES cell marker, green). As a control, the differentiated ES cells cultured in an untreated culture solution from d10 to d20 were used. Activin and the differentiated ES cells (B) on d40 were stained with Alb (hapatocyte cell marker, red) and Dolichos biflorus agglutinin (DBA) lectin (bile duct marker, green). The bar indicates 200 μm.

Moreover, in the present example, KhES-1 cells as human ES cells were cultured on M15 cells in the same manner as that for mouse ES cells. In the present example, it was demonstrated that, when M15 cells are used as supporting cells and a growth factor are combined therewith, KhES-1 expresses AFP and Alb in the same order as that in the mouse ES cells and it then differentiates into hepatic cells (FIG. 8).

Example 2

(A) Method
(1) Differentiation of Human ES Cells

As human ES cells, KhES-1 cells were inoculated on a 24-well or 6-well plate, on which M15 cells had previously been inoculated, at a density of 20,000 or 80,000 cells per well, respectively. The ES cells were cultured up to the $50^{th}$ day of culture in a differentiation medium (which was DMEM supplemented with 10% KSR, 4,500 mg/L glucose, NEAA, L-Glu, PS, and β-ME). From the d10 to d50, activin A (20 ng/ml) and LY294002 (10 µM) were added to the cells. From the $10^{th}$ to $50^{th}$ days, HGF (10 ng/ml) and Dex (1 µM) were added thereto. The medium was replaced with a fresh differentiation medium, to which a growth factor had been added, every two days.

(2) RT-PCR Analysis

RNA was extracted from the ES cells or mouse liver using RNeasy mini-kit (Qiagen), and it was then treated with DNase (Qiagen). Total RNA of the liver of a human fetus (22 to 40 weeks old) and that of the liver of an adult (51-year-old) were purchased from Clontech Laboratories, Inc. As a reverse transcription reaction, 3 µg of RNA was subjected to reverse transcription using MMLV reverse transcriptase (Toyobo) and oligo dT primers (Toyobo). A PCR analysis was carried out using 1 µl of 5-times diluted cDNA (1% of RT product). The primers of each primer set are shown in Table 2. As a real-time PCR analysis, mRNA expression was quantified using SyberGreen of ABI 7500 thermal cycler (Applied Biosystems). The expression level of each gene was standardized with the expression level of β-actin. PCR conditions were as follows. An operation consisting of denaturation at 95° C. for 15 seconds and annealing and elongation at 60° C. for 60 seconds was repeated for 40 cycles. Mean β-actin (mouse) and GAPDH (human) Ct values (limit cycles) were subtracted from the mean Ct values of each genes, so that each sample could be standardized in terms of β-actin (mouse) and GAPDH (human) in each measurement. Each target mRNA level (indicated by arbitrary unit) was obtained from a standard curve.

TABLE 2

Primers (SEQ ID NOS 25-40, respectively, in order of appearance) used in RT-PCR analysis for human ES cell-derived differentiated cells

| Gene | Forward primier | Reverse primier |
|---|---|---|
| Afp | TGCCAACTCAGTGAGGACAATCCAACAGGCCTGAGAAATC | |
| Alb | GATGTCTTCCTGGGCATGTTACATTTGCTGCCCACTTTTC | |
| Cyp3a4 | CAGGAGGAAATTGATGCAGTGTCAAGATACTCCATCTGTAGTTT | CACAGT |
| Cyp7a1 | AATTCCATACCTGGGCTGTGAGGCAGCGGTCTTTGAGTTA | |

TABLE 2-continued

Primers (SEQ ID NOS 25-40, respectively, in order of appearance) used in RT-PCR analysis for human ES cell-derived differentiated cells

| Gene | Forward primier | Reverse primier |
| --- | --- | --- |
| Gapdh | CGAGATCCCTCCAAAATCAACATGAGTCCTTCCACGATACCAA | |
| Oatp1b2 | TGAACACCGTTGGAATTGC | TCTCTATGAGATGTCACTGGAT |
| Oct4 | AGGTGTGGGGGATTCCCCC | GCGATGTGGCTGATCTGCTGCAT |
| Sox17 | ACTGCAACTATCCTGACGTGAGGAAATGGAGGAAGCTGTT | |

(3) Periodic Acid-Schiff (PAS) Analysis

The cultured cells were fixed with 3.3% formalin for 10 minutes. Intracellular glycogen was stained with a PAS staining solution (Muto Pure Chemicals) in accordance with an instruction manual.

(4) Albumin Secretion Analysis

The medium was replaced with a fresh one, and 24 hours later, the conditioned medium was recovered. Using Lebis ELISA kit (Shibayagi), albumin secretion was analyzed.

(5) Measurement of Cytochrome P450 3A Activity

In order to confirm cytochrome P450 3A activity, 3μg of a microsome sample was analyzed using P450-Glo™ CYP3A4 Assay Kit (Promega). The microsome was prepared from the liver of a 6-week-old male ICR mouse, undifferentiated ES cells, and differentiated ES cells. The content of a protein in microsome preparation was measured using Micro BCA™ Assay Kits (Pierce).

(B) Results (1) Efficiency of Differentiation Induction of Mouse and Human ES cell-derived hepatic Cells With regard to cells induced from mouse ES cells, albumin-expressing cells were quantified by an immunohistostaining method. The results are shown in Table 3. On d8, α-fetoprotein-positive cells existed at 33.1%. On the 30$^{th}$ day of differentiation, however, the percentage of the α-fetoprotein-positive cells was decreased to 7.4%. On the d30, the percentage of albumin-positive hepatocytes was approximately 18%, and DBA-positive bile duct cells was approximately 72%. Accordingly, it can be said that the ratio of differentiated cells was increased. With regard to human ES cells, on d20, AFP-positive cells were induced to differentiate at a high efficiency (80%) (Table 3). On d40$^t$, albumin-expressing hepatocytes existed at approximately 9%.

[Table 3]

Figure 9:
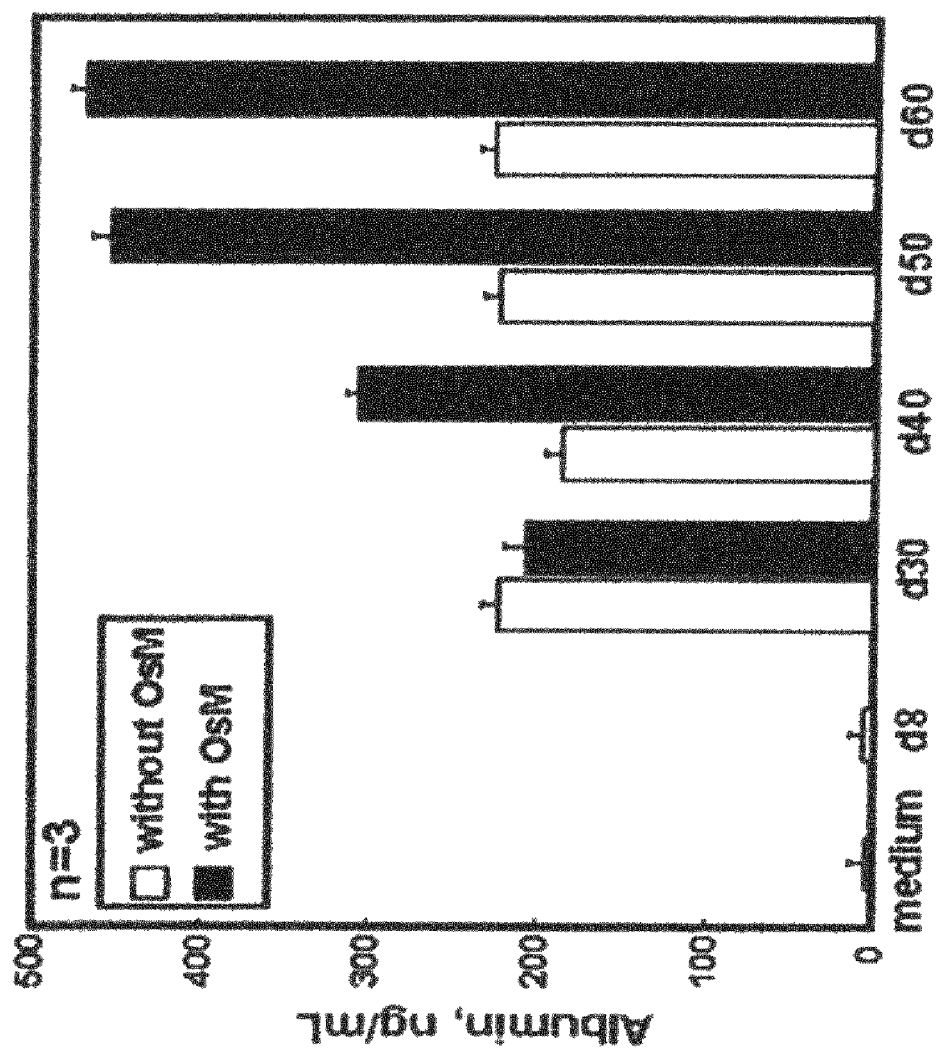
FIG. 9 shows the results obtained by analyzing the albumin secretory ability of ES cell-derived hepatocytes by ELISA. The differentiation medium was replaced with a fresh one 24 hours before the analysis. The amount of albumin released from the ES cell-derived hepatocytes to the medium for 24 hours was measured in each medium on the d8, d40, and d60.

(2) Albumin Secretory Ability of Mouse ES Cell-Derived Hepatic Cells (FIG. 9)

It has been reported that OsM induces maturation of mouse fetal liver cells (Kamiya, A., Kinoshita, T. & Miyajima, A. (2001) Oncostatin M and hepatocyte growth factor induce hepatic maturation via distinct signaling pathways. FEBS Lett 492, 90-94). Thus, the influence of OsM on albumin secretion was analyzed by ELISA. The results are shown in FIG. 9. The effect of OsM to enhance albumin secretion was not observed until c40. On d50 and d60, the medium supplemented with OsM, Dex and HGF was compared with a control medium to which only Dex and HGF had been supplemented, and as a result, it was found that albumin secretion was increased by 2 times in the differentiation medium to which OsM, Dex, and HGF had been supplemented.

Figure 10:
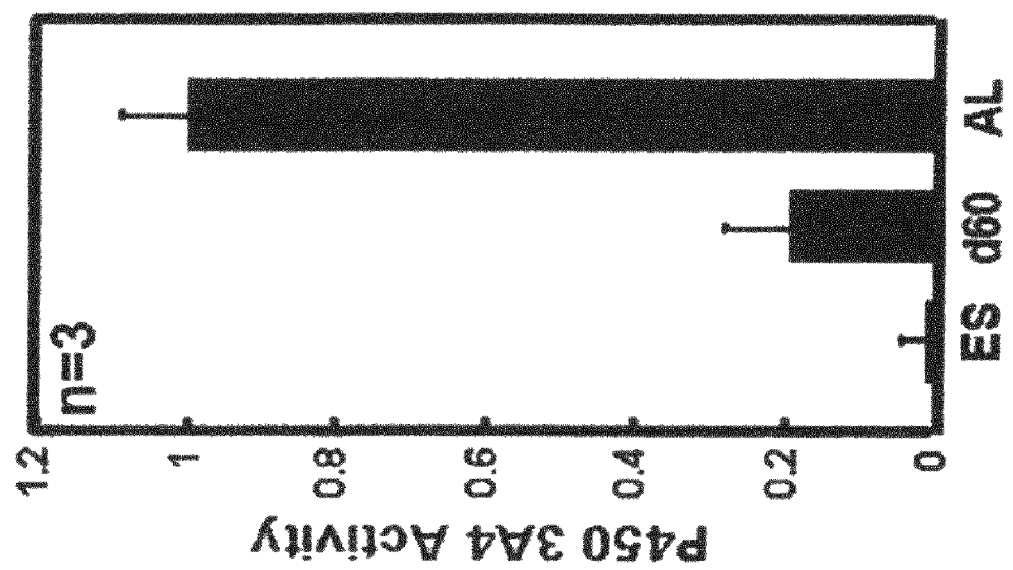
FIG. 10 shows the cytochrome P450 3A4 activity of ES cell-derived hepatic cells. Each value was standardized with protein amount. The graph shows a relative activity obtained in a case in which the activity of an adult liver is defined as 1. The term "ES" indicates undifferentiated ES cells; the term "d60" indicates the differentiated ES cells growing on M15 cells on day 60; and the term "AL" indicates an adult liver. Each value indicates a mean value ±standard error (n =3).

(3) P450 Enzyme Activity of Mouse ES Cell-Derived Hepatic Cells (FIG. 10)

Further, the enzyme activity of P450 enzyme Cyp3A was evaluated. The results are shown in FIG. 10. In the mouse ES cell-derived differentiated cells on d60, the enzyme activity of Cyp3A was approximately 1/5 of that of an adult (AL).

Figure 11:
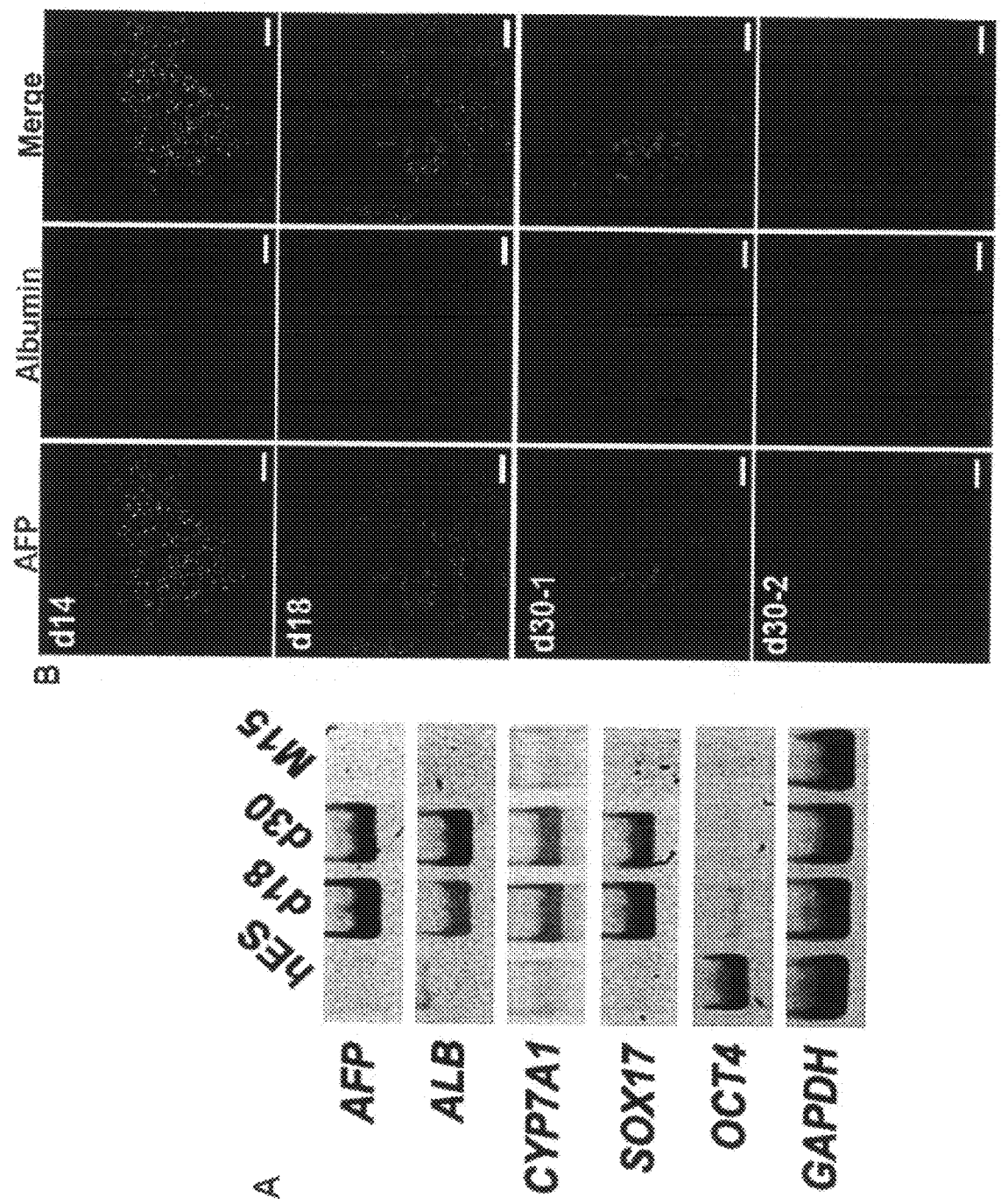
FIG. 11 shows the differentiation of human ES cells into hepatic cells. The differentiated human ES cells (KhES-1) on d10, which were allowed to grow on M15 cells to which 20 ng/ml activin, 10 μM LY294002, 10% KSR, and 4,500 mg/L glucose had been added. On the $10^{th}$ day, the additives were converted to 1 μM Dex and 10 ng/ml HGF.

(4) Expression Analysis of Molecular Markers in Hepatic Cells Obtained by Induction of Differentiation from Human ES Cells (FIG. 11)

FIG. 11 A shows the expression level of a transcript of endoderm or liver marker in human ES cell-derived differentiated cells (d18 and d30). An endoderm marker Sox17, Afp, Alb, and Cyp7a1 were detected in ES cells on the 18$^{th}$ day of differentiation. On d30, the expression of Afp decreased, and the expression of Alb significantly increased.

FIG. 11B shows that albumin-positive cells were detected on d18. Cells that expressed both AFP and albumin existed. On d30, cell colonies that did not express AFP and expressed only albumin were found.

Figure 12:
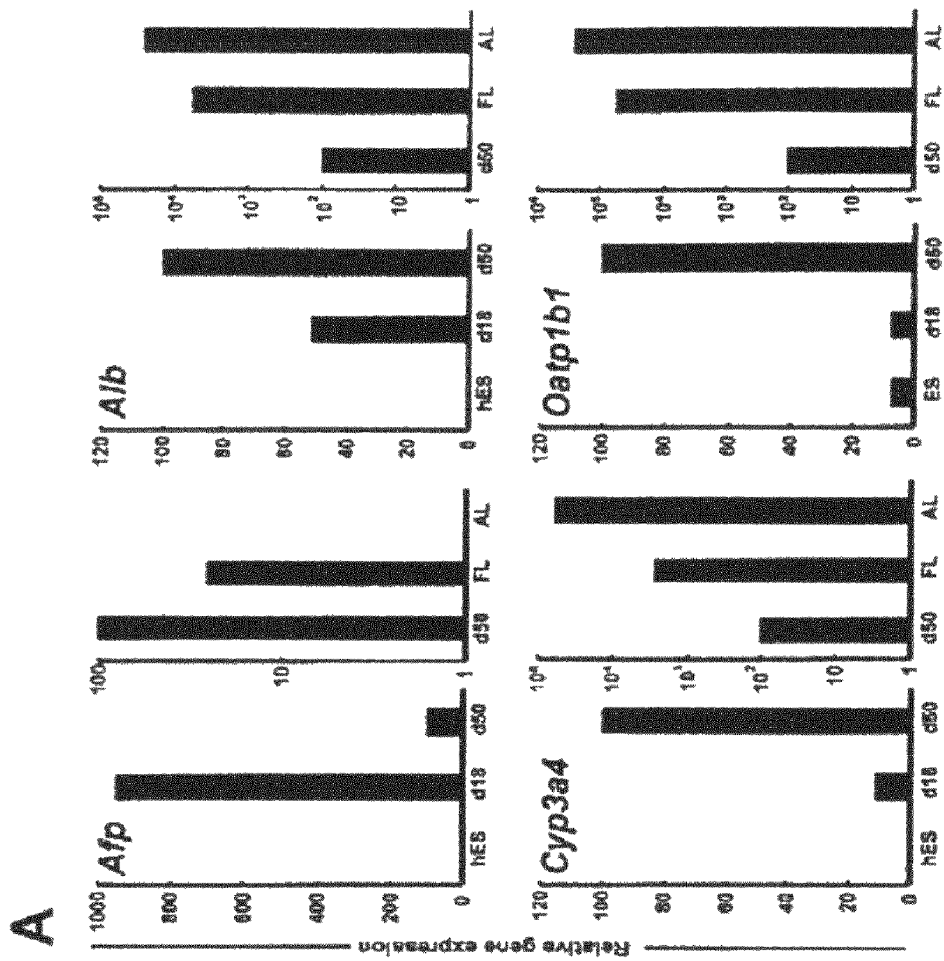
FIG. 12 shows the analysis of human ES cell-derived hepatocytes. The transcript of a hepatic marker gene was quantified by a real-time PCR analysis. The amount of the transcript was standardized with the amount of Gapdh. Each value was standardized with the value of the differentiated ES cells on the d50. The graph shows a relative gene expression level obtained when the value on d50 was defined as 100. The term "hES" indicates undifferentiated human ES cells; the terms d18 and d50 indicate that the differentiated ES cells were allowed to grow on M15 cells on $18^{th}$ and $50^{th}$ days of differentiation; the term "FL" indicates a human fetal liver (22 to 40 weeks old); and the term "AL" indicates a human adult liver (51 years old).

(5) Expression of Molecular Markers of Hepatic Cells Obtained by Induction of Differentiate from Human ES Cells (FIG. 12)

Human ES cell-derived hepatic cells expressed molecular markers for a mature liver. In order to examine the maturation level of such human ES cell-derived hepatic cells, liver molecular markers were analyzed by quantitative PCR using the cultures on d18 and d50. The results are shown in FIG. 12. In terms of the expression levels of such molecular markers, a 22- to 40-week-old fetal liver was compared with an adult liver. Afp was expressed on d18, and it was then decreased on d50. On d50, the expression level thereof in the adult liver was

TABLE 3

Quantitative analysis of hepatic cells which was differentiated from mouse and human ES cell

| | Mouse Es (%) | | | Human ES (%) | | |
| --- | --- | --- | --- | --- | --- | --- |
| Antigen | d8 | d30 | Antigen | d14 | d20 | d40 |
| AFP | 33.1 ± 1.7 | 7.4 ± 0.9 | Oct3/4 | 8.2 ± 0.9 | 0 | 0 |
| Albumin | 0 | 17.8 ± 1.3 | AFP | 40.4 ± 3.6 | 79.4 ± 2.8 | 58.5 ± 5.1 |
| DBA | 0 | 72.9 ± 3.8 | Albumin | 0 | 0.8 ± 0.1 | 9.0 ± 1.2 |

Data represent mean ± SEM of three samples.

much higher than that in the fetal liver. Mature liver cell markers such as albumin (Alb), Cyp3a4, and a liver-specific organic anion transport polypeptide 1B1 (Oatp1b1) (Konig, J., Cui, Y., Nies, A. T. & Keppler, D. (2000) A novel human organic anion transporting polypeptide localized to the basolateral hepatocyte membrane. Am J Physiol Gastrointest Liver Physiol 278, G156-164) were detected on d18, and thereafter, they increased to a considerable amount on d50.

(6) Human ES Cell-Derived Hepatic Cells are PAS-Positive (FIG. 13)

A majority of the differentiated human ES cells on d24 and d50 were PAS-positive, and they exhibited glycogen precipitation.

Figure 14:
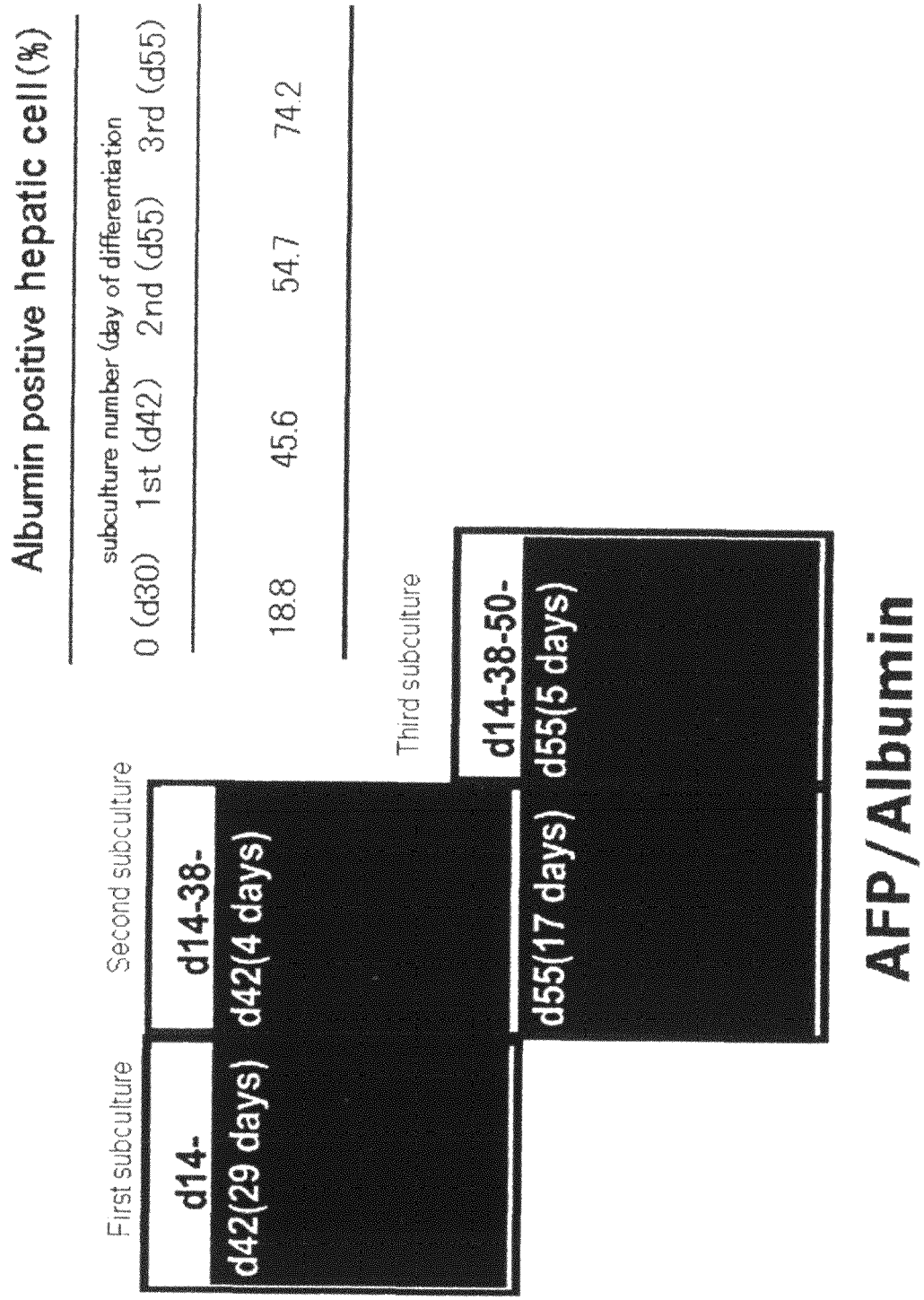
FIG. 14 shows an increase in the efficiency of differentiating into hepatic cells by subculture. When no subculture was carried out, the percentage of albumin-positive cells accounted for 18% of the total percentage. However, such percentage was successfully increased to 74.2% by repeating subculture. A first subculture was carried out on the d14, and a second subculture was then carried out 24 days after the subculture (the d38 from initiation of the culture). A third subculture was carried out 12 days after the second subculture (d50 from initiation of the culture). In all such subcultures, the cells that had been treated with trypsin and had been then recovered were 4-times diluted and were inoculated into fresh M15 cells. The days in the parentheses indicate the number of culture days after each subculture. The right table indicates the ratio of albumin-positive cells in each subculture.

(7) Increase in Efficiency of Differentiating into Differentiated Hepatic Cells by Subculture (FIG. 14)

The ratio of albumin-positive hepatocytes was increased by subculture on M15 cells.

The invention claimed is:

1. A method for inducing the differentiation of an ES cell into a hepatic cell, which comprises
   (a) culturing a mammal-derived ES cell on an M15 feeder layer in the presence of activin and bFGF, and then
   (b) culturing the cell obtained in (a) on an M15 feeder layer in the presence of dexamethasone, HGF, and oncostatin M to produce a hepatic cell.

2. The method according to claim 1, wherein BMP4 is further added to the culture comprising the mammal-derived ES cell and/or the culturing comprising the cell obtained in (a).

3. The method according to claim 1, wherein, after the ES cell has been cultured in the presence of activin and bFGF, the activin and bFGF are removed.

4. The method according to claim 1, wherein the mammal-derived ES cell is an ES cell derived from a mouse, a monkey, or a human.

5. A method for obtaining a hepatic cell by induction of differentiation from an ES cell, which comprises inducing the differentiation of a hepatic cell from an ES cell by the method according to claim 1, and separating the differentiation-induced hepatic cell by flow cytometry using fluorescence labeling.

* * * * *